(12) United States Patent
Ashgriz et al.

(10) Patent No.: US 12,245,918 B1
(45) Date of Patent: Mar. 11, 2025

(54) NEGATIVE PRESSURE BANDAGE

(71) Applicants: Nasser Ashgriz, Thornhill (CA);
Mojtaba Falahatinezhad, Maple (CA)

(72) Inventors: Nasser Ashgriz, Thornhill (CA);
Mojtaba Falahatinezhad, Maple (CA)

( * ) Notice: Subject to any disclaimer, the term of this patent is extended or adjusted under 35 U.S.C. 154(b) by 0 days.

(21) Appl. No.: 18/927,053

(22) Filed: Oct. 25, 2024

(51) Int. Cl.
*A61F 13/0206* (2024.01)
*A61F 13/05* (2024.01)

(52) U.S. Cl.
CPC .......... *A61F 13/0206* (2013.01); *A61F 13/05* (2024.01)

(58) Field of Classification Search
CPC ............ A61F 13/02; A61F 2013/00089; A61F 2013/00246; A61F 2013/0028; A61F 13/05; A61F 13/0203; A61F 13/0206; A61F 13/0209; A61M 1/90; A61M 1/91; A61M 1/915; A61M 1/962; A61M 1/964
See application file for complete search history.

(56) References Cited

U.S. PATENT DOCUMENTS

2008/0306456 A1* 12/2008 Riesinger ............ A61F 13/0203 604/316
2015/0202354 A1* 7/2015 Wall ...................... A61F 13/022 604/319

* cited by examiner

*Primary Examiner* — Susan S Su
*Assistant Examiner* — Erin A Kim
(74) *Attorney, Agent, or Firm* — Nasser Ashgriz

(57) ABSTRACT

A negative pressure wound therapy (NPWT) bandage is disclosed, comprising a bottom layer with a wound-contacting section and an adhesive section to secure to surrounding skin. The contacting section has apertures or an open area to allow fluid flow from the wound into the bandage. The top layer features deformable hollow domes made of resilient material and a central cavity above the wound. Integrated one-way valves direct fluid from the central cavity through the domes and out to the atmosphere, preventing reverse flow. By manually compressing the domes, a vacuum is created over the wound to facilitate NPWT. The domes automatically return to their original shape when the pressure falls below a predetermined threshold, promoting healing by maintaining negative pressure over the wound.

20 Claims, 26 Drawing Sheets

NEGATIVE PRESSURE BANDAGE

FIELD OF THE INVENTION

The present invention is a type of bandage and specifically a bandage that can provide negative pressure wound therapy.

BACKGROUND OF THE INVENTION

Negative pressure is a term used to describe a pressure that is below the normal atmospheric level of approximately 760 mmHg (about 1 bar) and can be achieved by removing air from a specific area of interest. It is well-established that application of a negative pressure on a wound can promote wound healing. This is referred to as Negative Pressure Wound Therapy (NPWT), which involves applying controlled sub-atmospheric pressures on a wound site, typically through a dressing and drainage tube connected to a vacuum pump. NPWT offers several benefits for wound healing, including increased blood flow to the wound site to help deliver oxygen and nutrients necessary for tissue repair, reduced edema (swelling) to improve blood flow, and reduced pain, promotion of new tissue to fill the wound bed during the healing process, and reduction of bacteria and debris from the wound. NPWT is particularly effective for chronic and hard-to-heal wounds, reducing the risk of scarring and infections following surgical incisions, and managing complex healing concerns.

Traditionally, NPWT devices have relied on bulky and cumbersome electric pumps. These pumps require a power source and can be inconvenient for patients, especially those who are mobile or require frequent dressing changes.

SUMMARY OF THE INVENTION

A novel bandage is disclosed that provides a negative pressure wound therapy over a wound. This bandage comprises of a bottom layer and a top layer. The bottom layer comprises of a contacting section that is configured to be placed on top of a wound and an adhesive section that is configured to sealably stick onto the skin surrounding the wound. A plurality of apertures is defined in the contacting section to allow fluid out of the wound and into the bandage. A fluid absorbing wound dressing is provided that is attached to the bottom side of the contacting section to absorb any exudate and liquids that come out of the wound. The top layer comprises of a central section located immediately above the contacting section of the bottom layer and a plurality of deformable hollow domes positioned above the adhesive section. These domes are made from a resilient material that returns to its original shape once they are forced to deform. A plurality of one-way valves are integrated into the bandage at the lower periphery of domes. The plurality of the one-way valves connects: the open cavity of the central section to the interior of one or more hollow domes; the interior of a dome to the interior of an adjacent dome, and the interior of a dome to the surrounding atmosphere. These valves are configured to provide one-way fluid flow from the central section to the atmosphere through the domes while preventing reverse fluid flow. When the domes are manually deformed, the air within them is squeezed out, and as they return to their original shape, a vacuum is created over the wound, providing a negative pressure wound therapy.

The domes have larger thickness in their periphery to restore the dome's shape under a predetermined pressure. The domes will return to their fully expanded configuration if the pressure differential between the dome's interior and the atmosphere falls below a predetermined threshold. However, when the pressure differential exceeds this threshold, the dome remains in a deformed state.

In one embodiment, each dome is semi-conical, featuring a substantially spherical base, with its apex aligned downstream of the one-way fluid flow and the base upstream. The domes may vary in size, with the largest dome located closest to the central section and the smallest dome adjacent to the atmosphere. The domes can be aligned linearly, in cross-linear formations, or in sets distributed around the contacting section.

The number and size of the domes can be designed to create a wide range of vacuums, such as 30 mm Hg to 120 mm Hg.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION

FIGS. 1A-D, 2, 3, and 4A-H show one embodiment of the present bandage. The Bandage 100 comprises of two main components: a bottom layer 120 configured to be placed over the wound and the skin surrounding the wound, and a top layer 110. The top layer 110 and the bottom layer 120 are adhered to each other by a medical adhesive forming an integrated bandage. The Bandage 100 is configured to provide a negative pressure wound therapy over the wound, thereby assisting in the healing process. The negative pressure described herein is a pressure below atmospheric pressure.

Figure 2:
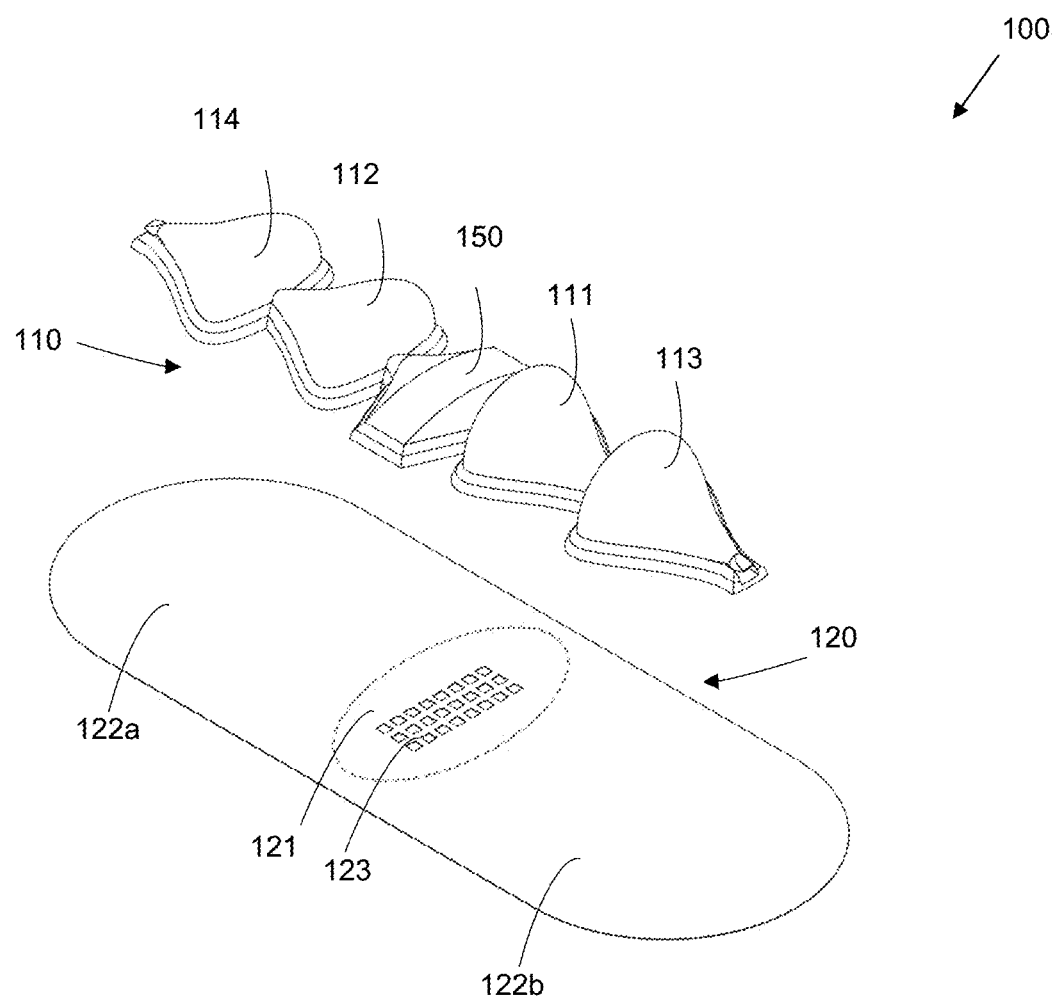
FIG. 2 shows an exploded view of the embodiment of the invention.

FIG. 2 shows an exploded view of the embodiment of the presently disclosed bandage. The bottom layer 120 consists of a contacting section 121 and an adhesive section 122. The contacting 121 section is designed to be placed on top of the wound and the adhesive section 122 is designed to stick onto the skin surrounding the wound to keep the bandage 100 securely in place and prevent air from entering the wound. In one embodiment, as shown in FIG. 2, the adhesive section 122 comprises two sides: a first side 122a and a second side 122b, with each side extending outward from the contacting section 121. In this configuration, the bottom layer 120 forms a round ended rectangular shape with the contacting section 121 positioned in the middle of the bottom layer 120. An open area, or a plurality of apertures 123 are defined within the contacting section 121 to allow fluid from the wound to pass through the contacting section 121.

As shown in FIGS. 1A, 1B, 1C, and 2, the top layer 110 comprises a central section 150 positioned immediately above the contacting section 121 and a plurality of deformable hollow domes 111, 112, 113, and 114 positioned immediately above the adhesive section 122. The central section 150 is a hollow dome, which can have any shape base, such as a hexagonal base, and it is made of a stiff material to keep an open cavity space 151 above the wound. The plurality of the hollow domes 111, 112, 113, and 114 are in a semi-conical shape with a substantially semi-spherical shape base. These domes are made of a flexible and resilient material, so that they can be deformed by pressing on them and then they tend to return to their original shape once they are not pressed on. In one embodiment, as shown in FIG. 2, the plurality of deformable hollow domes, 111, 112, 113, and 114, comprises of two sets of domes: a first set of domes and a second set of domes, arranged in a linear alignment on the first and second side of the contacting section 122a and 122b, respectively. The first set and the second set of domes are in linear alignment with respect to each other. The central section 150 is positioned in the middle of this alignment. In one embodiment of the bandage 100, the plurality of deformable hollow domes 111, 112, 113, and 114 comprises of four domes, with each set of domes including two domes. The first set of domes includes a first inner dome 111 positioned adjacent to the central section 150 and a first outer dome 113 adjacent to the first inner dome 111. The second set includes a second inner dome 112 positioned adjacent to the central section 150 and a second outer dome 114 adjacent to the second inner dome 112.

The central section 150 of the top layer 110 can be made of rigid polycarbonate material to keep the open cavity space 151 above the wound. The bottom layer 120 and the plurality of domes 111, 112, 113, and 114 are selected from a group consisting of rubber, silicone, silicone blends, silicone substitutes, polyvinyl chloride, polystyrene, polypropylene, polyurethane, polyester, vinyl, polyimide, polyethylene napthalate, polycarbonates, polyester-polycarbonate blends, or a similar polymer, and combinations of all such materials.

Figure 1A:
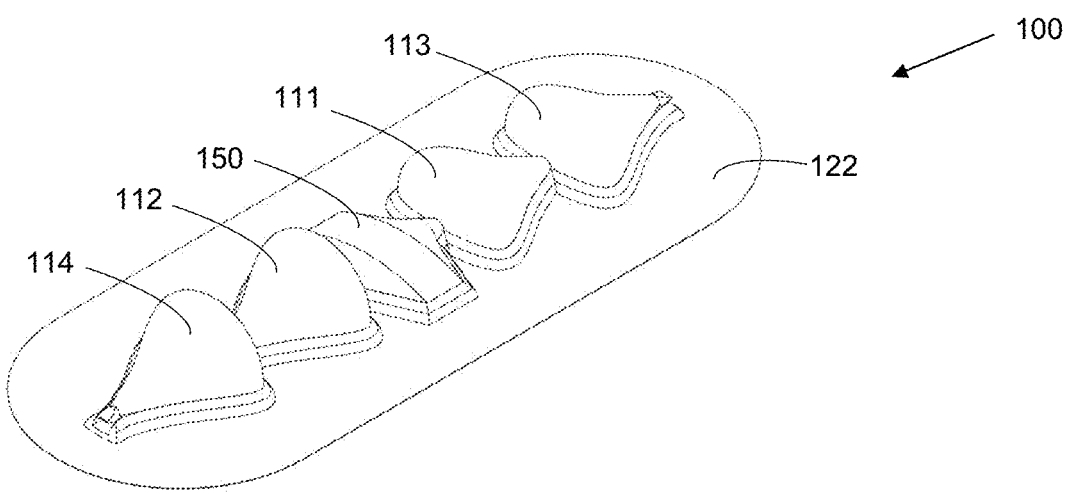
FIG. 1A shows an isometric view of one embodiment of the invention.
Figure 1B:
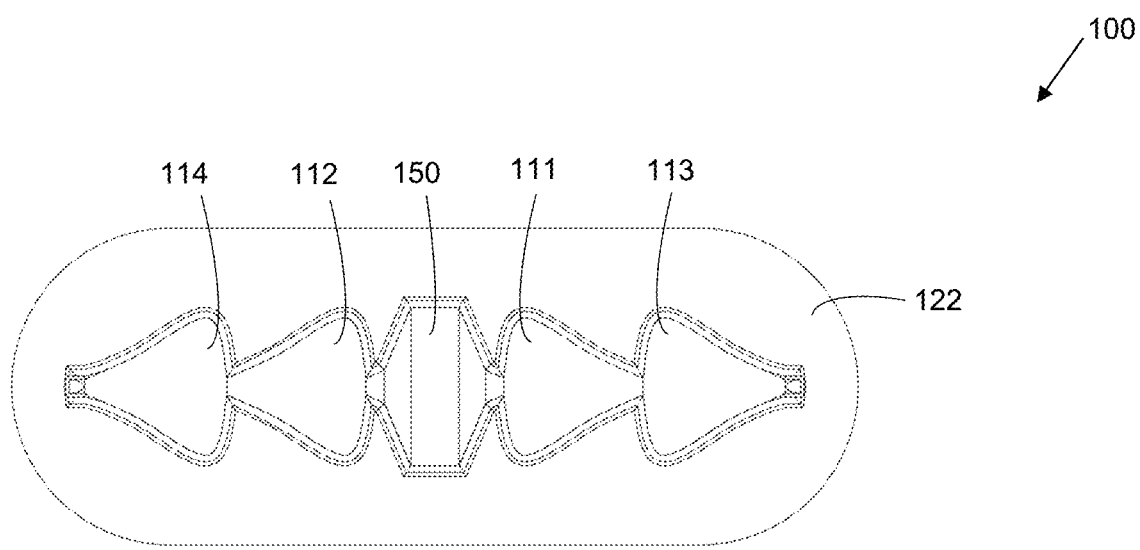
FIG. 1B shows a top view of the embodiment of the invention.
Figure 1C:
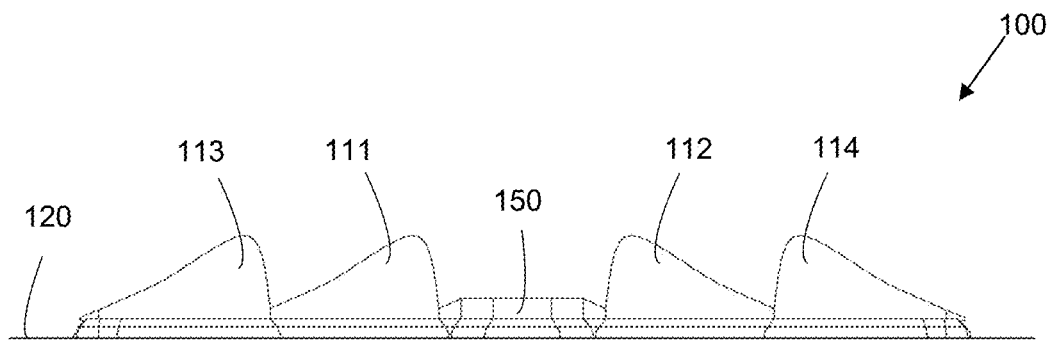
FIG. 1C shows a side view of the embodiment of the invention.
Figure 1D:
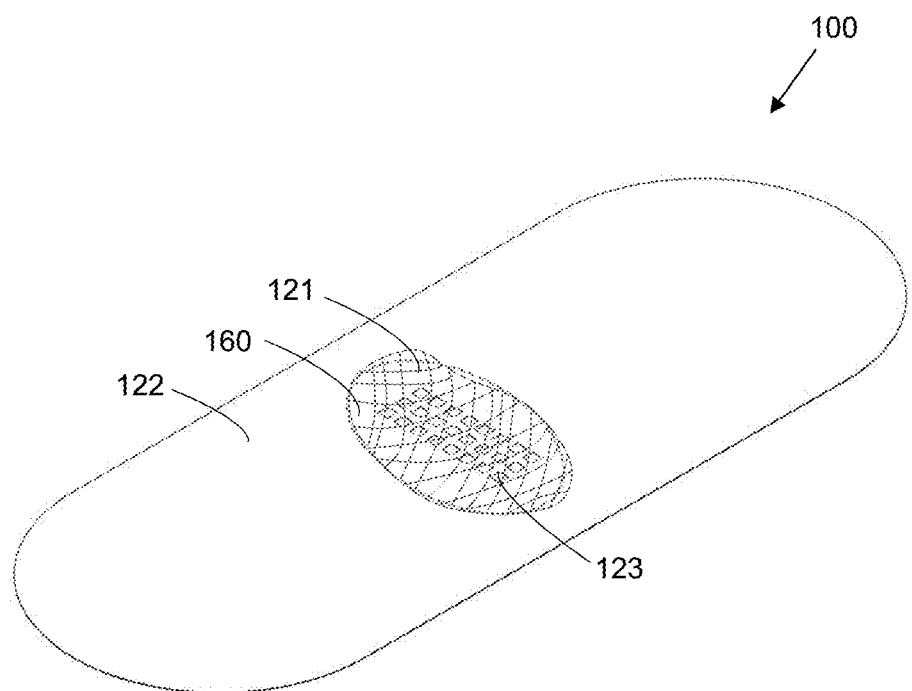
FIG. 1D shows a bottom view of the embodiment of the invention.

FIG. 1D shows a bottom view of the bandage 100. A wound dressing 160 is attached to the bottom side of the contacting section 121, positioned between the contacting section 121 and the wound. The dressing 160 comprises a liquid absorbing material to absorb wound exudate and liquids that come out of the wound and is configured to allow for even distribution of negative pressure across the wound surface without creating barriers that could obstruct pressure transmission to the wound. Additionally, it provides structural support for cell migration and tissue regeneration under negative pressure. The dressing can be chosen from absorbent dressing, antiseptic dressing, nonadherent dressing, water dressing, absorbable matrix, gauze, foam, or combinations thereof.

Figure 3:
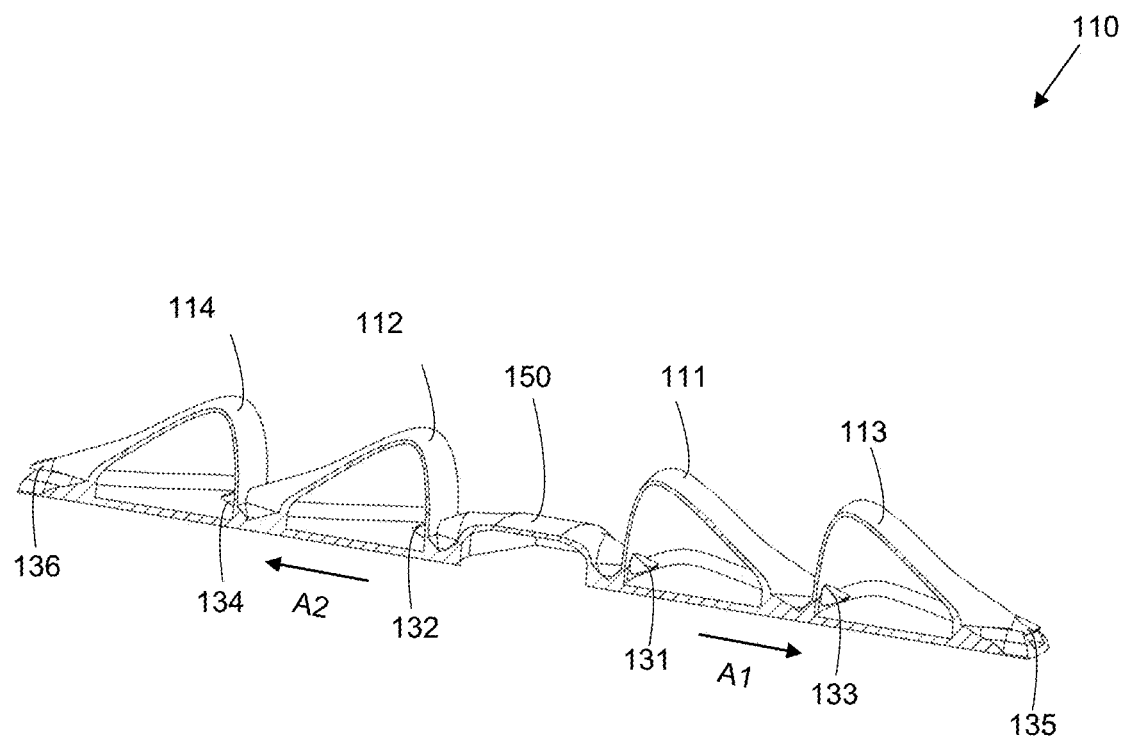
FIG. 3 shows an isometric cross-sectional view of top layer of the embodiment of the invention.

FIG. 3 shows an isometric cross-sectional view of the top layer 110 of the embodiment of the bandage 110. By pressing onto the domes and sliding a finger from the inner domes 111 and 112 to the outer domes 113 and 114, fluid flows are directed from the open cavity space 151 to the surrounding atmosphere: a fluid flows from central section through the first set of domes 111 and 113, and a fluid flows from the central section through the second set of domes 112 and 114, creating two pathways for fluid transfer from the central section 150 to the surrounding atmosphere. A1 and A2 illustrate the direction of the one-way fluid flow through the first set of domes 111 and 113, and the second set of domes 112 and 114, respectively. A plurality of one-way valves 131, 132, 133, 134, 135, and 136 is integrated into the bandage 100, providing one-way fluid flow from the open cavity space 151 of the central section 150 to the surrounding atmosphere passing through each of the set of domes, separately. The one-way fluid flow described herein indicates that fluid flows outward from the central section 150 to the surrounding atmosphere, without any reverse flow from surrounding atmosphere into the open cavity space 151.

The central section 150 is connected to the first inner dome 111 via a one-way valve 131, the first inner dome 111 is connected to the first outer dome 113 via a one-way valve 133, and the first outer dome 113 is connected to the surrounding atmosphere via a one-way valve 135. The one-way valves 131, 133, and 135 enable one-way fluid transfer from the open cavity space 151 of the central section 150 into the internal space of the first inner dome 111, from the internal space of the first inner dome 111 into the internal space of the first outer dome 113, and from the internal space of the first outer dome 113 into the surrounding atmosphere, respectively, while preventing any fluid communication in the reverse direction. Similarly, the central section 150 is connected to the second inner dome 112 via a one-way valve 132, the second inner dome 112 is connected to the second outer dome 114 via a one-way valve 134, and the second outer dome 114 is connected to the surrounding atmosphere via a one-way valve 136. The one-way valves 132, 134, and 136 enable one-way fluid transfer from the open cavity space 151 of the central section 150 into the internal space of the second inner dome 112, from the internal space of the second inner dome 112 into the internal space of the second outer dome 114, and from the internal space of the second outer dome 114 into the surrounding atmosphere, respectively, while preventing any fluid communication in the reverse direction.

Again, as shown in FIGS. 1A, 1B, 1C, 2, and 3 the plurality of the hollow domes are in a semi-conical shape with a substantially semi-spherical base. In this configuration, the apex is on the downstream side of the fluid flow and the semi-spherical base is on the upstream side of the fluid flow. A1 and A2 in FIG. 3, illustrate the direction of the fluid flow through the first and second sets of domes 112 and 114, respectively. The one-way valves integrated into the apex of domes work as an outlet valve for the respective dome and the one-way valves integrated into the spherical base aligned with the apex works as an inlet valve for the respective dome. For instance, the valve 131 connecting the first inner dome 111 to the first outer dome 113 works as an outlet valve for the first inner dome 111 and works as an inlet valve for the first outer dome 113. The operating pressure of a one-way valve indicates the minimum pressure difference required between the inlet and outlet sides of the valve for it to open. Once this pressure differential is reached, the valve allows fluid to flow through. In one embodiment of the invention, the operating pressure of the valves 131-136 increases in the direction of the fluid flow A1 and A2 with the valves 131 and 132 connecting the central section 150 to the inner domes 111 and 112 having the smallest operating pressure and the valves 135 and 136 connecting the outer domes 113 and 114 to the surrounding atmosphere having the greatest operating pressure. The result of this is that the one-way valves 135 and 136 connecting the outer domes 113 and 114 to the surrounding atmosphere open in higher pressure difference than the one-way valve 131 and 132 connecting the central section 150 to the inner domes 111 and 112.

Figure 4A:
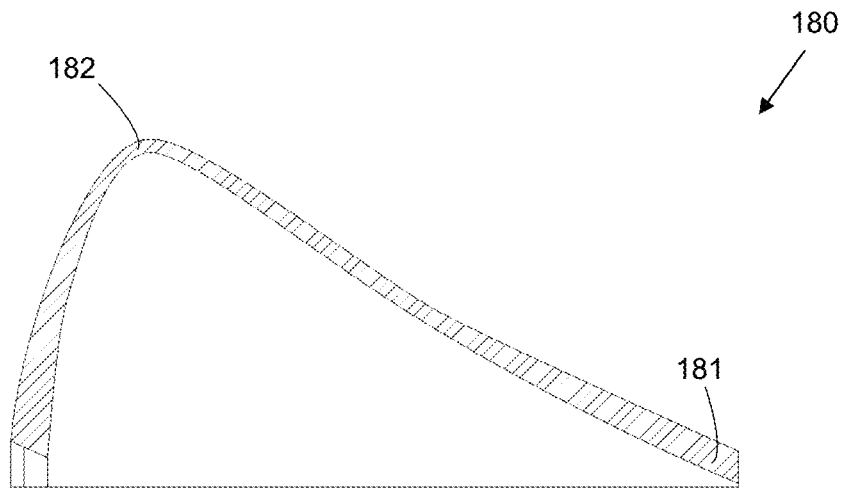
FIG. 4A shows a cross-sectional view of a dome from a plurality of the domes.

FIG. 4A shows a cross-sectional view of one dome 180 from the plurality of hollow domes in one embodiment of the bandage. The conical shape naturally concentrates pressure as it narrows toward the apex 181. By pressing the top of the dome 182, the force is directed through the smaller outlet at the apex 181. As the cone narrows, the applied force becomes more focused at the apex 181, resulting in greater pressure that expels fluid more efficiently with minimal effort from the user. This increase in pressure also helps open one-way valve at the apex 181 when there is a higher-pressure differential, allowing the valve's operating pressure to be set higher, which reduces the risk of one-way valves' leakage. Additionally, the domes are designed for easy finger operation, enabling smooth movement from one dome to the next. The leakage described herein and in this patent, indicates any fluid communication in the reverse direction of the fluid flow.

Figure 4B:
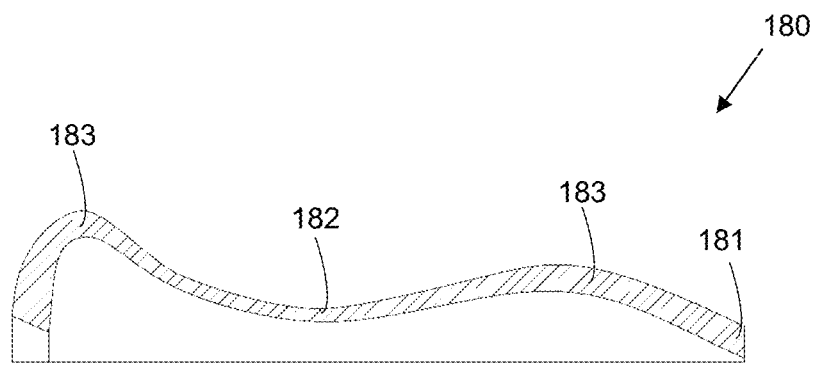
FIG. 4B shows a cross-sectional view of a dome from a plurality of the domes when it is being pressed.

FIGS. 4A and 4B, show cross-sectional views of one dome 180 from the plurality of hollow domes in one embodiment of the bandage in a fully expanded state (FIG. 4A) and a fully compressed state (FIG. 4B), respectively. The fully expanded state describes the state where the deformable dome 180 is in its original shape and the fully compressed state describes the state where the deformable dome 180 is pressed down to its minimum volume or flattened configuration. The thickness of dome 180 is non-uniform, with the periphery of the dome 180 having the largest thickness, and the thickness decreasing progressively towards the top of the dome 182. The thickness is directly related to the dome's elasticity, with the periphery 182 having the highest elasticity and the top 182 having the least. As a result, the periphery 180 of the dome is more resistant to deformation compared to the top 182. When the dome 180 is pressed, the top of the dome 182 deforms and becomes concave. Due to the top of the dome's thinness, it deforms under low pressure, making it easy to press. The increased thickness of the periphery 182 prevents complete deformation of the dome 180 by maintaining its structural integrity. The knee of the dome 183, defined as the transition point where the dome begins to concave, undergoes the most reshaping compared to both the periphery and the top 182. The thick material in this region provides high elasticity and resilience, allowing it to absorb energy when the dome 180 is pressed and help the dome 180 return to its original form once the applied pressure is removed. The thickness of the dome 180 in this region is designed to restore the dome's 180 shape under a predetermined pressure. When the pressure differential between the interior of the dome 180 and atmospheric pressure falls below a predetermined range, the dome 180 returns to its fully expanded state. If the pressure differential is within the predetermined range, the dome 180 partially expands; as the pressure differential increases, the extent of expansion decreases. When the pressure differential exceeds the predetermined range, the dome 180 does not expand further and remains in a deformed configuration.

FIGS. 5A-E show a side cross-sectional view of the embodiment of the bandage 100. The present device 100 can apply negative pressure to a wound by evacuating a portion of the air from the open cavity space 151 of the central section 150 through the domes 111, 112, 113, and 114 and one-way valves 131-136. By applying manual pressure to the top of the domes 111, 112, 113, and 114 and quizzing the air out of the domes 111, 112, 113, and 114, starting from the inner domes 111 and 112 to the outer domes 113 and 114, the domes 111-114 are deformed to their fully compressed state 14, 24, 34, and 44. The inner domes 111 and 112 evacuate into their adjacent outer domes 113 and 114, and the outer domes 113 and 114 evacuate into the surrounding atmosphere. The plurality of deformable domes 111, 112, 113, and 114 are made of elastic materials and want to return to their fully expanded state 11, 21, 31, and 41. While the domes 111-114 are expanding, the volume of the air inside the domes 111, 112, 113, and 114 increases, therefore their pressure decreases. Due to the pressure difference between the outer domes 113 and 114 and their adjacent inner domes 111 and 112 and between the inner domes 111 and 112 and the central section 150, their respective one-way valves 131, 132, 133, and 134 open and allow a portion of air from the inner domes 111 and 112 transfer to their adjacent outer domes 113 and 114, and a portion of air from the open cavity space 151 of the central section 150 transfer to the inner domes 111 and 112. Therefore, the pressure inside the central section 150 reduces. The reduced pressure described herein is a pressure below atmospheric pressure.

Figure 5A:
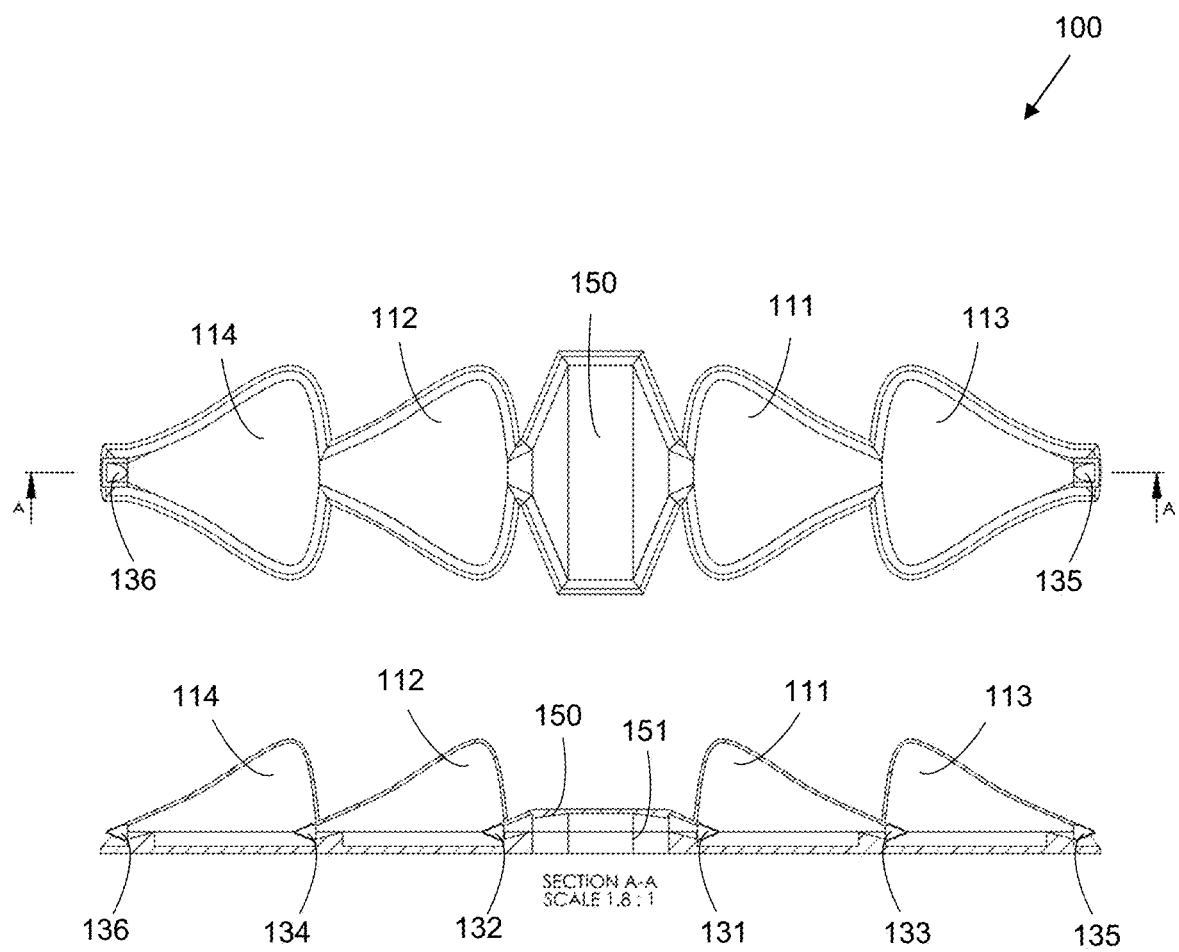
FIG. 5A shows a cross-sectional view of the embodiment of the invention.

In FIG. 5A, the plurality of domes 111, 112, 113, and 114 are in their fully expanded state and are not manually deformed yet. The pressure inside the domes 111, 112, 113, and 114 and the central section 150 is balanced with the surrounding atmospheric pressure, and all pressures are equal. The pressure of the first inner dome 111 $P_{fi}$, second inner dome 112 $P_{si}$, first outer dome 113 $P_{fo}$, second outer dome 114 $P_{so}$, and central section 150 $P_{center}$ are described herein for one embodiment of the bandage: $P_{fi}=P_{si}=P_{fo}=P_{so}=P_{center}=0$ mmHg. The pressure assigned to each of the plurality of the domes 111, 112, 113, and 114 and the central section 150 indicates the difference between the surrounding atmospheric pressure and the internal pressure of the domes 111, 112, 113, and 114 and the open cavity space 151 of the central section 150. These differential pressures are expressed in millimeters of mercury (mmHg).

Figure 5B:
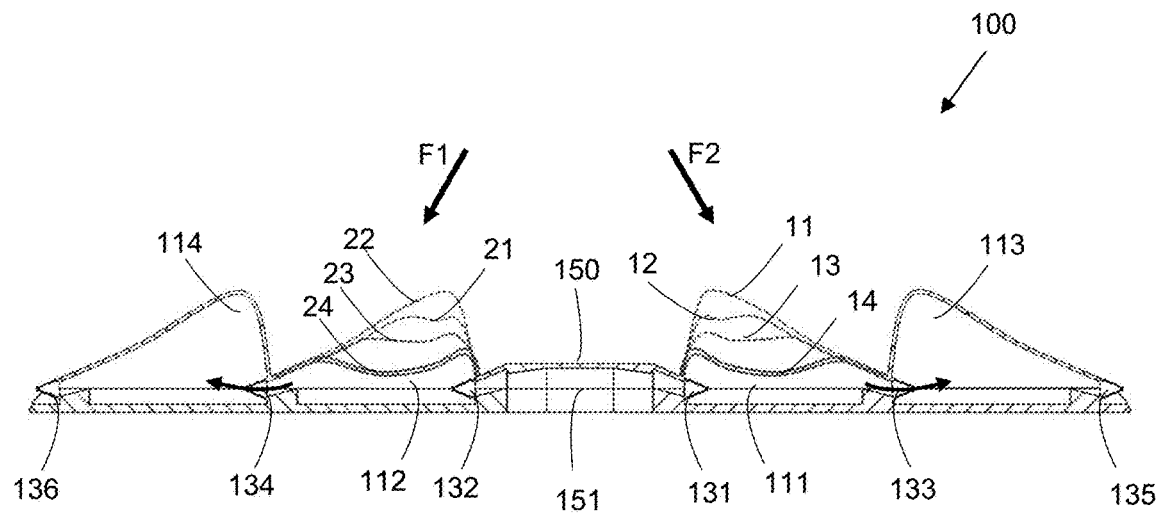
FIG. 5B shows a cross-sectional view of the embodiment of the invention when the inner domes are pressed.
Figure 5C:
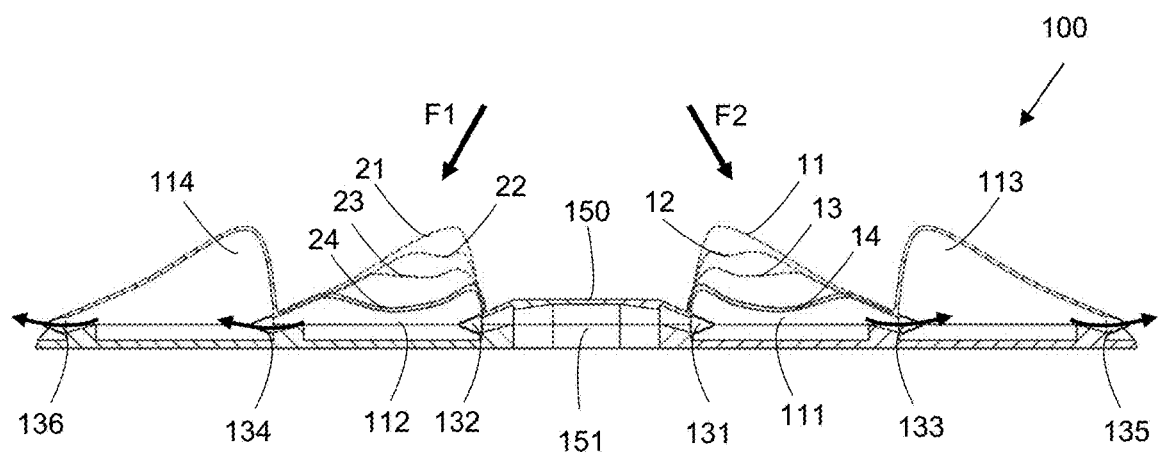
FIG. 5C shows another cross-sectional view of the embodiment of the invention when the inner domes are pressed

FIGS. 5B and 5C show the first inner dome 111 and the second inner dome 112 being pressed in the F1 and F2 directions. By pressing the first inner dome 111, it transitions from a fully expanded state 11 to partially compressed states 12 and 13 and eventually reaches a fully compressed state 14, resulting in a decrease in the volume of the first inner dome 111 and an increase in the pressure of the first inner dome 111 throughout this transition. As the pressure of the first inner dome 111 increases, it exceeds the pressure in the first outer dome 113. When the pressure difference between the first inner dome 111 and first outer dome 113 reaches the operating pressure of their respective one-way valve 133, said one-way valve 133 opens, allowing air within the first inner dome 111 to transfer into the first outer dome 113 (FIG. 5B). This fluid transfer causes a decrease in the pressure of the first inner dome 111 and an increase in the pressure of the first outer dome 113. Thereby, the pressure of the first outer dome 113 becomes higher than the surrounding atmospheric pressure. When the pressure difference between the first outer dome 113 and surrounding atmosphere reaches the operating pressure of their respective one-way valve 135, said one-way valve opens 135, allowing air within the first outer dome 113 to transfer to the surrounding atmosphere (FIG. 5C). Once the pressure differences between the first inner dome 111 and first outer dome 113 and between the first outer dome 113 and surrounding atmosphere becomes lower that the operating pressure of their respective valves 133 and 135, said valves 133 and 135 close, stopping the fluid transfer. A similar process occurs with the second inner dome 112 and the second outer dome 114. By pressing the second inner dome 112, it transitions from a fully expanded state 21 to partially compressed states 22 and 23 and eventually reaches a fully compressed state 24, resulting in a decrease in its volume and an increase in its pressure, that leads to a fluid transfer from the second inner dome 112 to the second outer dome 114 and from the second outer dome 114 to the surrounding atmosphere through their respective one-way valves 134 and 136 until their pressures balance and the valves 134 and 136 close.

For example, in one embodiment based on the Ideal Gas relationship, if the valves 133, 134, 135, and 136 do not open, the pressures when the inner domes 111 and 112 are fully compressed are described as follows: $P_{fo}=P_{so}=P_{center}=0$ mmHg, and $P_{fi}=P_{si}=+40$ mmHg. In one embodiment, at the end of the process described in FIGS. 5B and 5C, the pressures when the valves 133, 134, 135, and 136 close are described as follows: $P_{fo}=P_{so}=+3$ mmHg, $P_{fi}=P_{si}=+1$ mmHg, and $P_{center}=0$ mmHg.

Figure 5D:
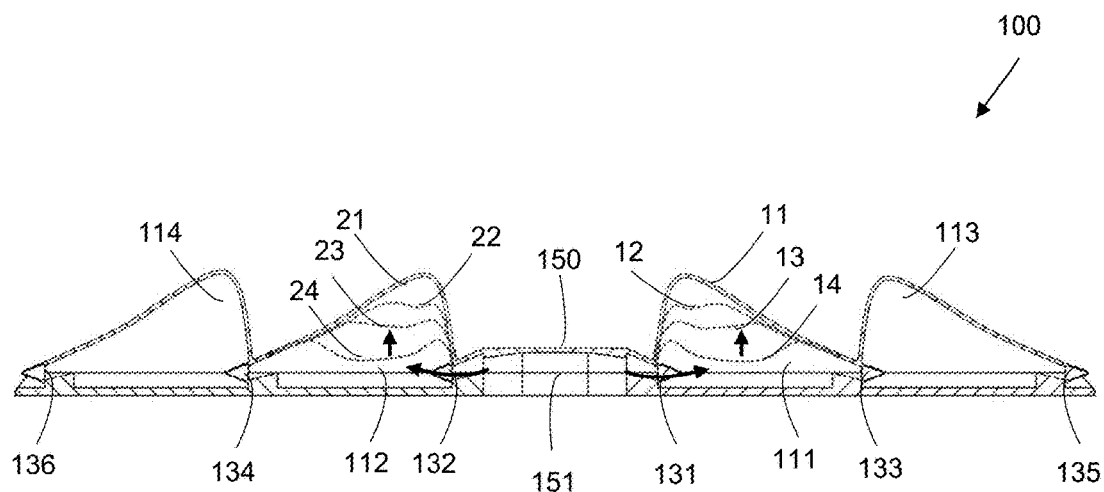
FIG. 5D shows a cross-sectional view of the embodiment of the invention when the inner domes are expanding.

The domes 111-114 are made of elastic materials and want to return to their fully expanded configuration. FIG. 5D illustrates the expansion of the pressed inner domes 111 and 112. The first inner dome 111 transitions from its fully compressed state 14 to partially compressed states 12 and 13 and eventually reaches the fully expanded state 11, which results in an increase in its volume and a decrease in its pressure throughout this transition. This decrease in pressure causes the pressure of the first inner dome 111 to become lower than the pressure in the open cavity space 151 of the central section 150. When the pressure difference between the open cavity space 151 and the first inner dome 111 reaches the operating pressure of their respective one-way valve 131, said one-way valve 131 opens, allowing air within the open cavity space 151 to transfer into the first inner dome 111. This fluid transfer causes a decrease in the pressure of the open cavity space 151 and an increase in the pressure of the first inner dome 111. Once the pressures difference between the open cavity space 151 and the first inner dome 111 becomes lower that the operating pressure of their respective valves 131, said valve 131 closes, stopping the fluid transfer. A similar process occurs with the second inner dome 112, where its expansion leads to an increase in its volume and a decrease in its pressure, resulting in fluid transfer from the open cavity space 151 to the second inner dome 112 through their respective one-way valve 132 until their pressures balance and the valve 132 closes. This process results in a reduction of the pressure in the open cavity space 151 of the central section 150 by both the first and second inner domes 111 and 112, creating a negative pressure over the wound.

For example, in one embodiment, if the said valves 131 and 132 do not open, the pressures when the inner domes 111 and 112 are fully expanded are described as follows: $P_{fo}=P_{so}=+3$ mmHg, $P_{fi}=P_{si}=-40$ mmHg, $P_{center}=0$ mmHg. In one embodiment, at the end of the process described in FIG. 5D, the pressures when the valves 131 and 132 close are described as follows: $P_{fo}=P_{so}=+3$ mmHg, $P_{fi}=P_{si}=-27$ mmHg, and $P_{center}=-26$ mmHg.

Figure 5E:
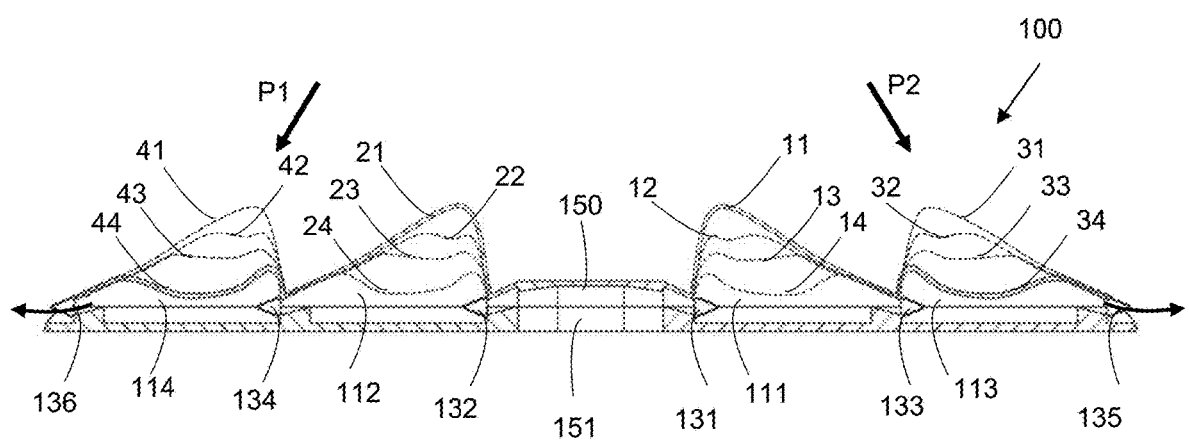
FIG. 5E shows a cross-sectional view of the embodiment of the invention when the outer domes are pressed.

FIG. 5E shows the first outer dome 113 and the second outer dome 114 being pressed in the P1 and P2 directions. Based on the time between pressing the inner domes 111 and 112 and outer domes 113 and 114, while the outer domes 113 and 114 are pressed, the inner domes 111 and 112 can be in a partially compressed state 12, 13, 22, and 23 and expanding to reach their fully expanded states 14 and 24 or be in their fully expanded state 14 and 24 already. By pressing the first outer dome 113, it transitions from its fully expanded state 34 to its partially compressed state 32 and 33 and eventually reaches its fully compressed 34, resulting in a decrease in its volume and an increase in its pressure throughout this transition. This pressure increase causes the pressure within the first outer dome 113 to become higher than the surrounding atmosphere's pressure. When the pressure difference between the first outer dome 113 and surrounding atmosphere reaches the operating pressure of their respective one-way valve 135, said one-way valve 135 opens, allowing air within the first outer dome 113 to transfer to surrounding atmosphere. This fluid transfer causes a decrease in the pressure of the first outer dome 113. Once the pressure difference between the first outer dome 113 and surrounding atmosphere becomes lower that the operating pressure of their respective valves 135, said valve 135 closes, stopping the fluid transfer. A similar process occurs with the second outer dome 114, where pressing it leads to its transition from a fully expanded state 41 to partially compressed states 42 and 43 and eventually a fully compressed state 44, resulting in fluid transfer from the second outer dome 114 to the surrounding atmosphere through its respective one-way valve 136 until its pressures balance and the valve closes 136.

For example, in one embodiment, if the said valves 135 and 136 do not open, the pressures when the outer domes 113 and 114 are fully compressed are described as follows: $P_{fo}=P_{so}=+40$ mmHg, $P_{fi}=P_{si}=-27$ mmHg, and $P_{center}=-26$ mmHg. In one embodiment, at the end of the process described in FIG. 5E, the pressures when the valves 113 and 114 close are described as follows: $P_{fo}=P_{so}=+3$ mmHg, $P_{fi}=P_{si}=-27$ mmHg and $P_{center}=-26$ mmHg.

Figure 5F:
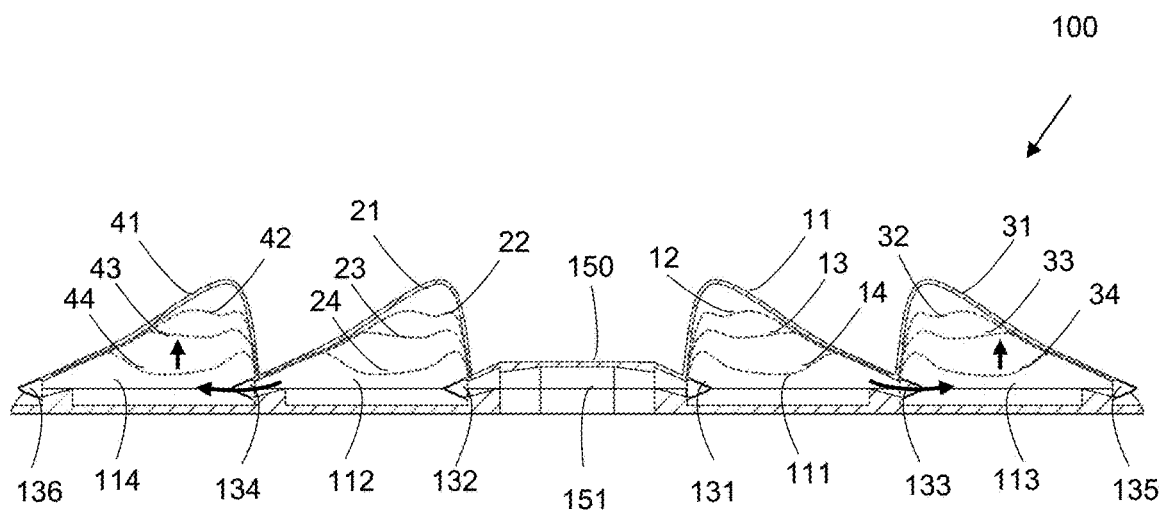
FIG. 5F shows a cross-sectional view of the embodiment of the invention when the outer domes are expanding.
Figure 5G:
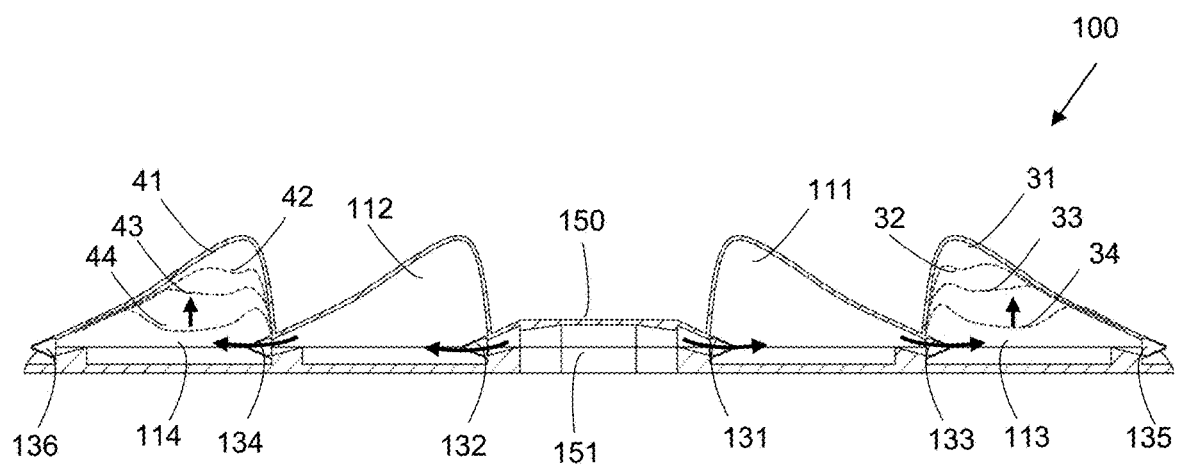
FIG. 5G shows another cross-sectional view of the embodiment of the invention when the outer domes are expanding.

FIGS. 5F and 5G illustrate the expansion of the pressed outer domes 113 and 114. Based on the time between pressing the inner domes 111 and 112 and outer domes 113 and 114, while the outer domes 113 and 114 are expanding, the inner domes 111 and 112 can be in a partially compressed state 12, 13, 22, and 23 and expanding to reach their fully expanded states 14 and 24 or being in fully expanded state 14 and 24 already. The first outer dome 113 transitions from its fully compressed state 34 to its partially compressed states 32 and 33 and eventually reaches to its fully expanded state 34, which results in an increase in its volume and a decrease in its pressure throughout this transition. This decrease in pressure causes the pressure of the first outer dome 113 to become lower than the pressure of the first inner dome 111. When the pressure difference between the first inner dome 111 and first outer dome 113 reaches the operating pressure of their respective one-way valve 133, said one-way valve 133 opens, allowing air within the first inner dome 111 to transfer into the first outer dome 113 (FIG. 5F). This fluid transfer causes a decrease in the pressure of the first inner dome 111 and an increase in the pressure of the first outer dome 113. The pressure decrease of the first inner dome 111 causes a pressure difference between the open cavity space 151 and the first inner dome 111. When the pressure difference between the open cavity space 151 and the first inner dome 111 reaches the operating pressure of their respective one-way valve 131, said one-way valve 131 opens, allowing air within the open cavity space 151 to transfer into the first inner dome 111 (FIG. 5G). Once the pressure differences between the first inner dome 111 and first outer dome 113 and between the first outer dome 113 and surrounding atmosphere becomes lower that the operating pressure of their respective valves 131 and 133, said valves 131 and 133 close, stopping the fluid transfer. A similar process occurs with the second outer dome 114, where its expansion leads to an increase in its volume and a decrease in its pressure, resulting in fluid transfer from the second inner dome 112 to the second outer dome 114 through their respective one-way valve 134. The fluid transfer causes a pressure increase in the second outer dome 114 and a pressure decrease in the second inner dome 112, resulting in fluid transfer from the open cavity space 151 of the central section 150 to the second inner dome 112 through their respective one-way valve 132. The fluid transfers keep happening until the pressure differences become lower than the operating pressure of the valves 132 and 134, and the valves 132 and 134 close. This process results in a reduction of the pressure in the open cavity space 151 of the central section 150 by both the first set of domes 111 and 113 and the second set of domes 112 and 114, increasing the negative pressure inside the open cavity space 151 and over the wound.

For example, in one embodiment, if the valves 131, 132, 133, and 134 do not open, the pressures when the outer domes 113 and 114 are fully expanded, are described as follows: $P_{fo}=P_{so}=-40$ mmHg, $P_{fi}=P_{si}=-27$ mmHg, and $P_{center}=-26$ mmHg.

In one embodiment, at the end of the process described in FIGS. 5F and 5G, the pressures when the valves close 131, 132, 133, and 134 are described as follows: $P_{fo}=P_{so}=-34$ mmHg, $P_{fi}=P_{si}=-31$ mmHg, and $P_{center}=-30$ mmHg.

Figure 5H:
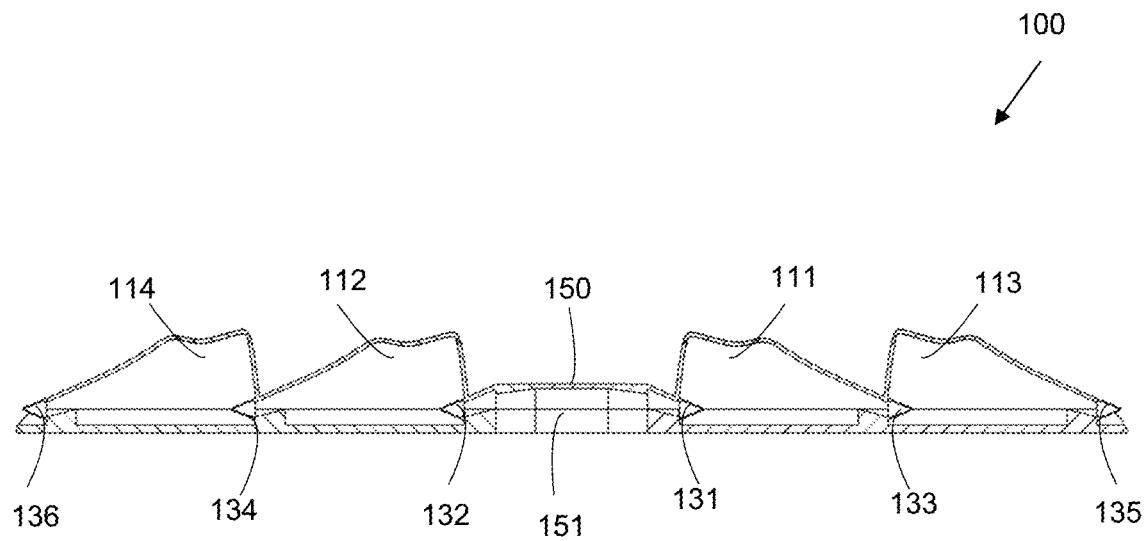
FIG. 5H shows a cross-sectional view of the embodiment of the invention when the domes partially expand.

By repeating the process, a negative pressure up to 120 mmHg lower than atmosphere is achievable. The domes 111, 112, 113, and 114 reshape as long as their pressure is within the predetermined pressure. In one embodiment, the predetermined pressure range is between 50 to 120. FIG. 5H shows the domes 111, 112, 113, and 114 expanded after being pressed in one of the repeating processes. In this embodiment, the pressure differential between the pressure inside of each dome 111, 112, 113, and 114, and atmospheric pressure is within the predetermined range; therefore, the domes 111, 112, 113, and 114 expand partially. For example, in one embodiment, at the end of this process, the pressures when the valves 131-136 close are described as follows: $P_{fo}=P_{so}=-64$ mmHg, $P_{fi}=P_{si}=-61$ mmHg, and $P_{center}=-60$ mmHg.

Figure 5I:
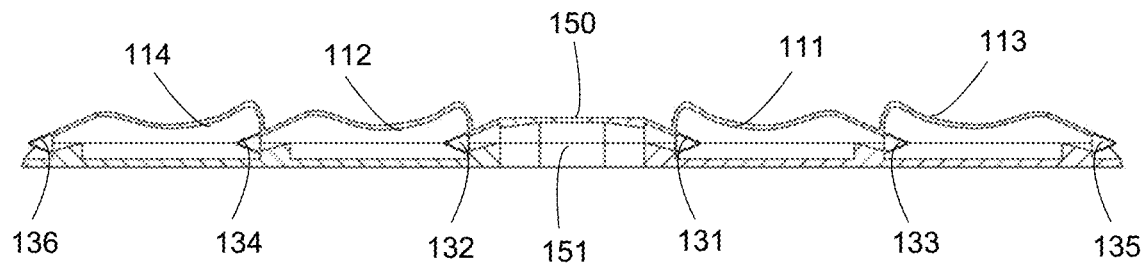
FIG. 5I shows a cross-sectional view of the embodiment of the invention when the domes remain pressed.

FIG. 5I shows the bandage 100 when the pressure differential between the pressure inside of each dome 111, 112, 113, and 114, and atmospheric pressure exceeds the predetermined range; therefore, the domes 111, 112, 113, and 114 remain in their fully compressed state. For example, in one embodiment, at the end of this process, the pressures when the valves 131-136 close are described as follows: $P_{fo}=P_{so}=-124$ mmHg, $P_{fi}=P_{si}=-121$ mmHg, and $P_{center}=-120$ mmHg.

Due to the different operating pressures of the valves 131-136, the pressure within the domes 111, 112, 113, and 114 decreases as we move from the inner domes 111 and 112 to the outer domes 113 and 114. The multi-dome design allows to use one-way valves with different operating pressures, which helps reduce the chances of leakage and infection.

In other embodiments of the device, the size of the bandage and the deformable hollow domes, the size and shape of the central section, the size and shape of the bottom layer can vary, and the configuration of the bandage can also differ in terms of the number and arrangement of domes. This allows for adaptability in their setup to meet the specific requirements of different applications.

Figure 6:
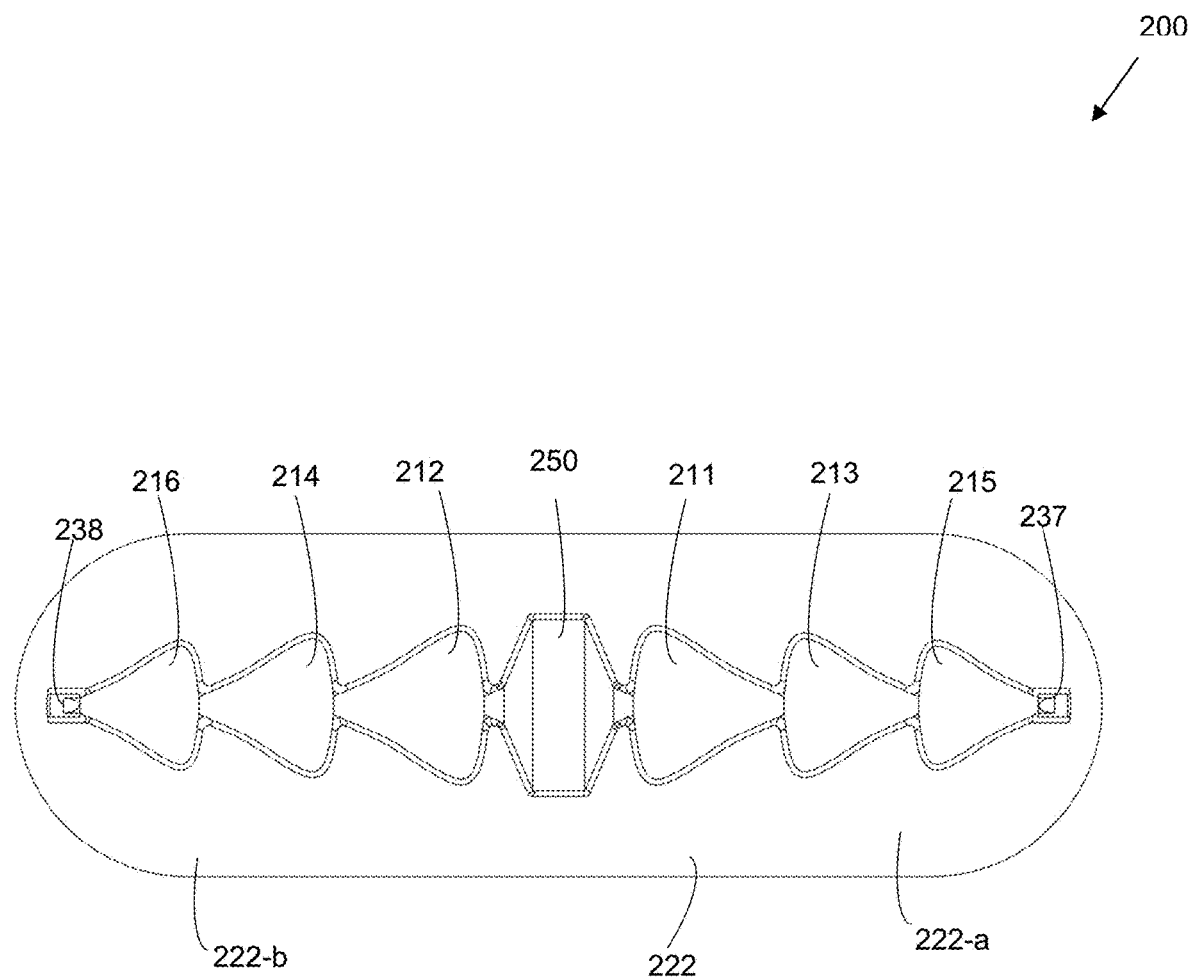
FIG. 6 shows a top view of another embodiment of the bandage.

FIG. 6 shows a top view of another embodiment of the bandage 200. In this embodiment of the bandage 200, the plurality of deformable hollow domes comprises six domes 211, 212, 213, 214, 215, and 216, with each of the first set of domes 211, 213, 215 and the second set of domes 212, 214, 215, and 216 including three domes arranged linearly on a first side 222-*a* and second side 222-*b* of the adhesive section 222, respectively. The size of the domes 211, 212, 213, 214, 215, and 216 in each set of domes reduces in the fluid flow direction with the largest domes 211 and 212 being adjacent to the central section 250 and the smallest domes 215 and 216 being positioned at the outermost ends of the alignment adjacent to the surrounding atmosphere through their respective one-way valves 237 and 238. The size reduction of the domes 211, 212, 213, 214, 215, and 216 in the fluid flow direction makes it easier for users to push and slide their finger on domes 211, 212, 213, 214, 215, and 216 from center to sides, from the biggest domes 211 and 212 toward the smallest domes 215 and 216. The possibility of leakage by adding the number of domes decreases. Besides, adding the number of domes allows to use one-way valves with higher operating pressures, which helps reduce the chances of leakage and infection.

Figure 7:
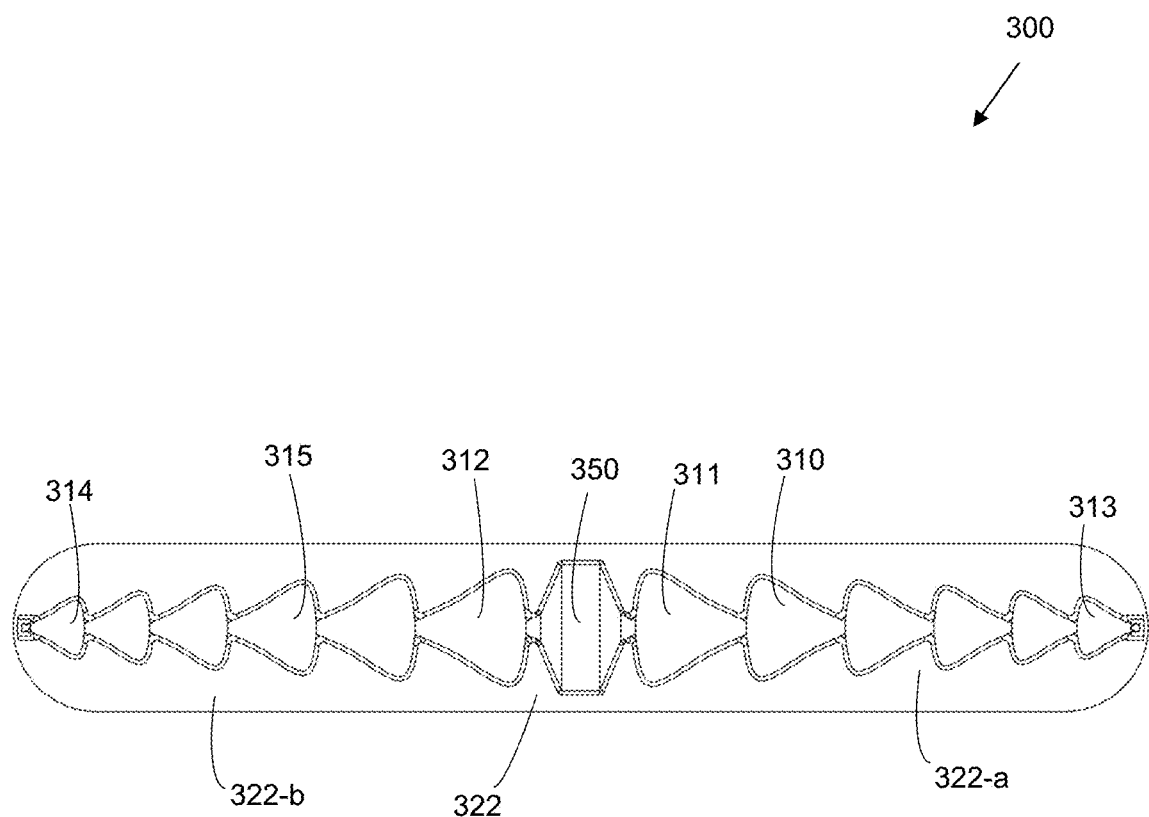
FIG. 7 shows a top view of another embodiment of the bandage.

FIG. 7 show another embodiment of the bandage 300 that the plurality of deformable hollow domes comprises twelve domes, with each of the first set of domes 310 and second set of domes 315 including six domes arranged linearly on the first side 322-*a* and second side 322-*b* of the adhesive section 322, respectively. Similar to the embodiment described in FIG. 6, the sizes of the domes in each first and second set of domes 310 and 315 reduce in the fluid flow direction with the largest domes 311 and 312 being adjacent to the central section 350 and the smallest domes 312 and 313 being positioned at the outermost ends of the alignment adjacent to the surrounding atmosphere. The operating pressure of the one-way valves integrated into the bandage 300 increases in the fluid flow direction.

The length of the adhesive section increases by adding the domes in each set of domes and by increasing the diameter of the domes. Based on the size of the wound and the negative pressure required for the wound the diameter and number of domes can be defined and the length of the adhesive section can be adjusted.

Figure 8A:
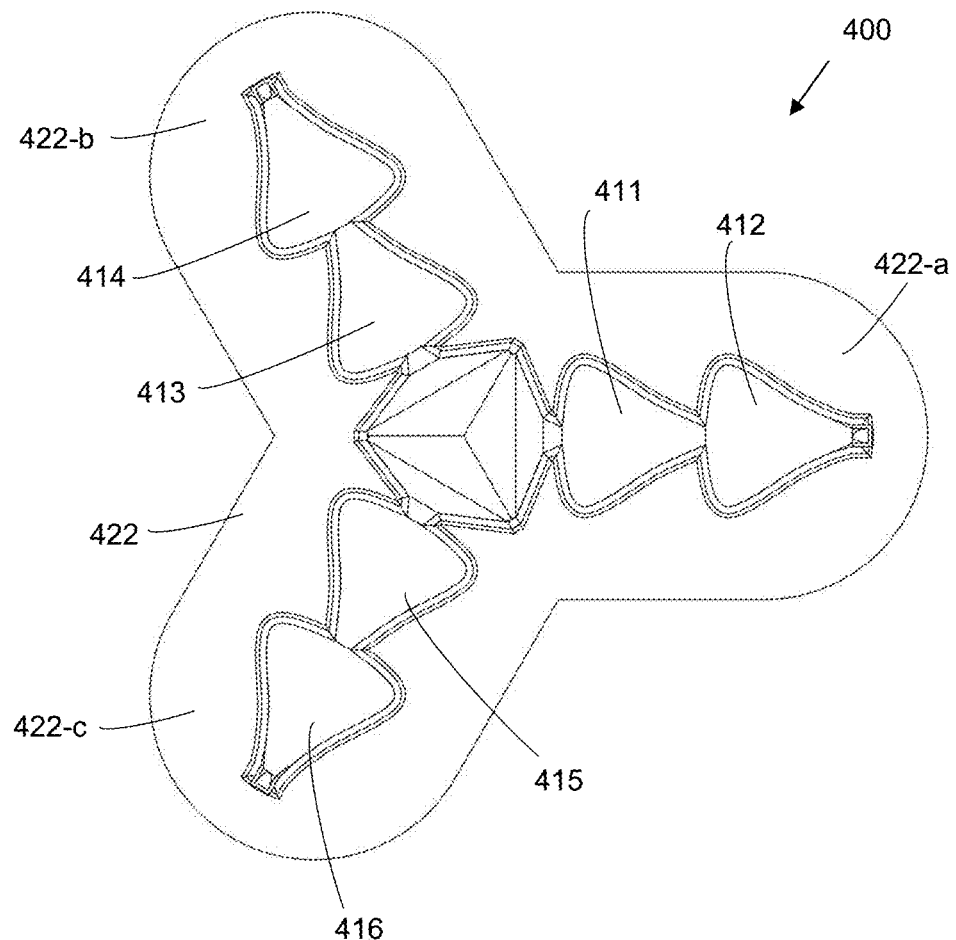
FIG. 8A shows a top view of another embodiment of the bandage.
Figure 8B:
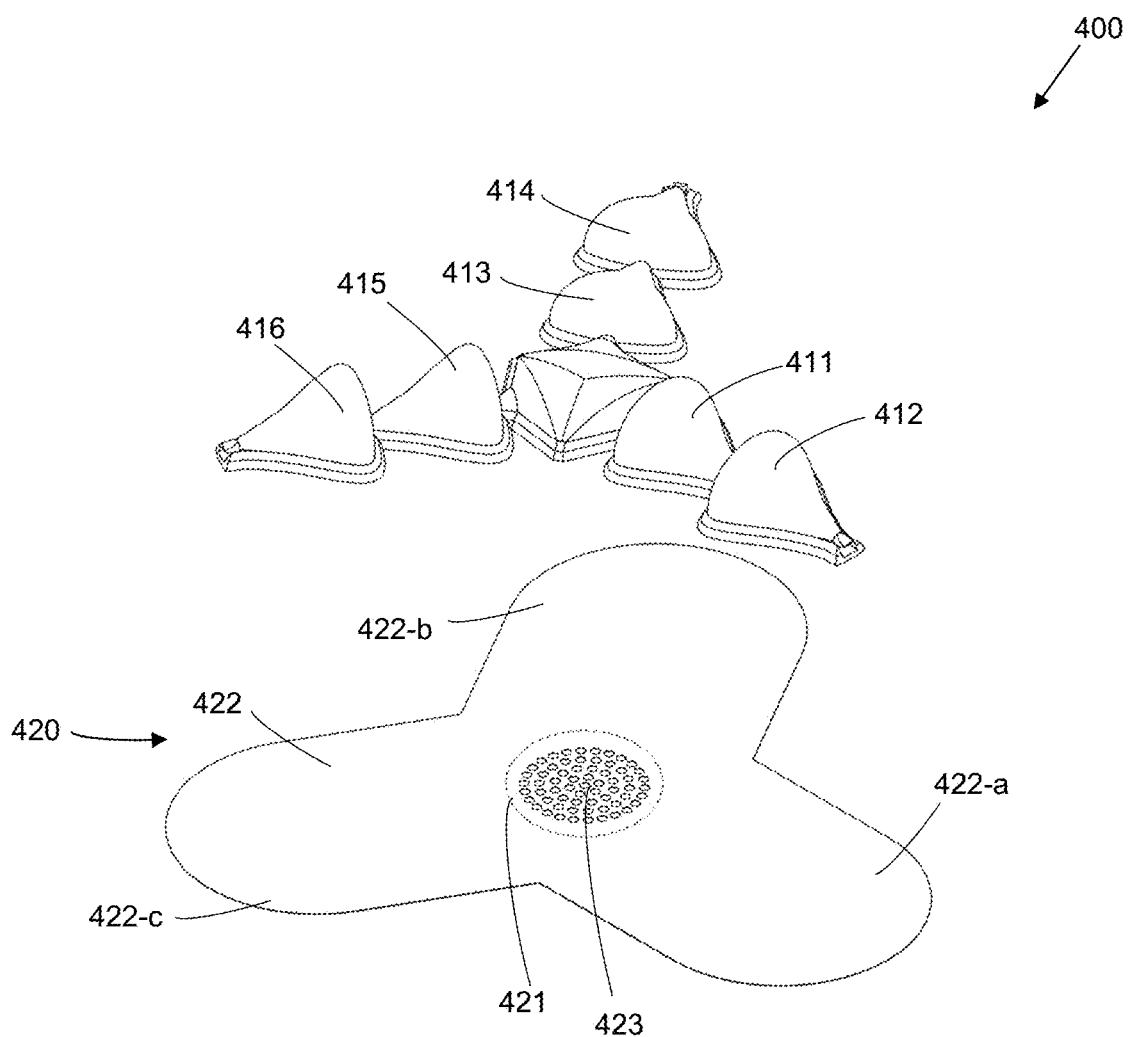
FIG. 8B shows an exploded view of another embodiment of the bandage.

FIGS. 8A, and 8B show top view and an exploded view of another embodiment of the bandage 400, respectively. In this embodiment, the adhesive section 422 comprises three sides: a first side 422-*a*, a second side 422-*b*, and a third side 422-*c* with each side extending outward from the contacting section 421. In this configuration, the bottom layer 420 forms a three-pointed star arrangement with the contacting section 421 positioned in the middle of the bottom layer 420 and the first side 422-*a*, the second side 422-*b*, and the third side 422-*c* each defining 120 degrees with respect to each other. A plurality of apertures 423 are defined within the contacting section 421 with circular configuration to allow fluid from the wound to pass through the contacting section 421. The plurality of deformable hollow domes 411, 412, 413, 414, 415, and 416 comprises three set of domes: a first set of domes 411 and 412, a second set of domes 413 and 414, and a third set of domes 415 and 416 arranged on the first 422-*a*, second 422-*b*, and third 422-*b* side of the contacting section 421, respectively. In one embodiment of the bandage, the plurality of deformable hollow domes comprises six domes 411, 412, 413, 414, 415, and 416, with each set of domes including two domes. This embodiment provides stability on angular body parts like elbow, knee and on other movement joints of body, where its focused adhesion points ensure the bandage remains securely in place during movement.

Figure 9:
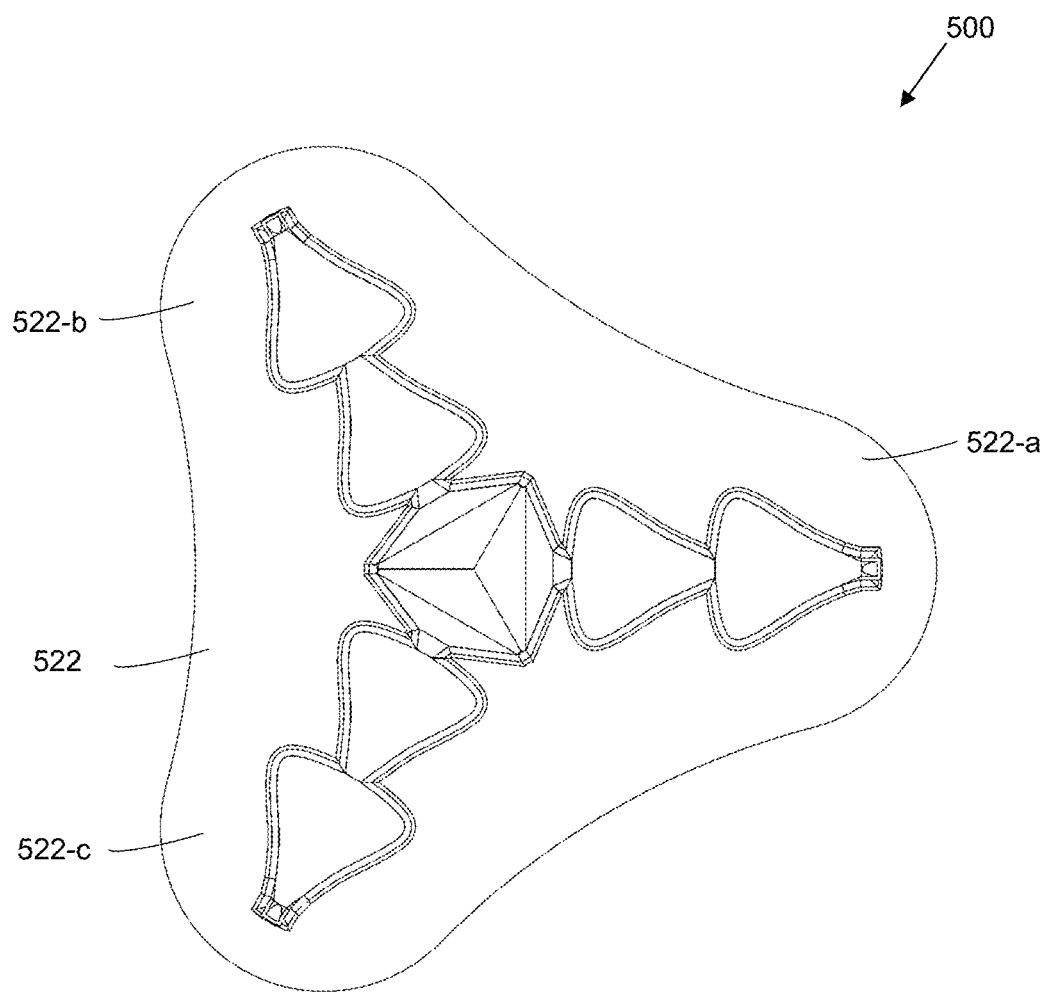
FIG. 9 shows a top view of another embodiment of the bandage.

FIG. 9 shows another embodiment of the bandage 500. This embodiment is similar to the embodiment described in FIGS. 8A and 8B, with the difference that unlike sharp transitions between the three outward-extending sides of the adhesive section 522 of the namely designed, in this design each of the first 522-*a*, second 522-*b*, and third sides 522-*c* is smoothly connected to the adjacent sides through curved, continuous transitions, forming a more expansive adhesive surface. The smooth transitions between the sides 522-*a*, 522-*b*, and 522-*c* increase the overall surface area of the adhesive section, creating a more uniform and rounded shape, which enhances adherence and stability. This design conforms well to the body's contours, allowing for better flexibility and a more effective seal. This embodiment fits better in areas such as the neck, shoulders, and back.

Figure 10:
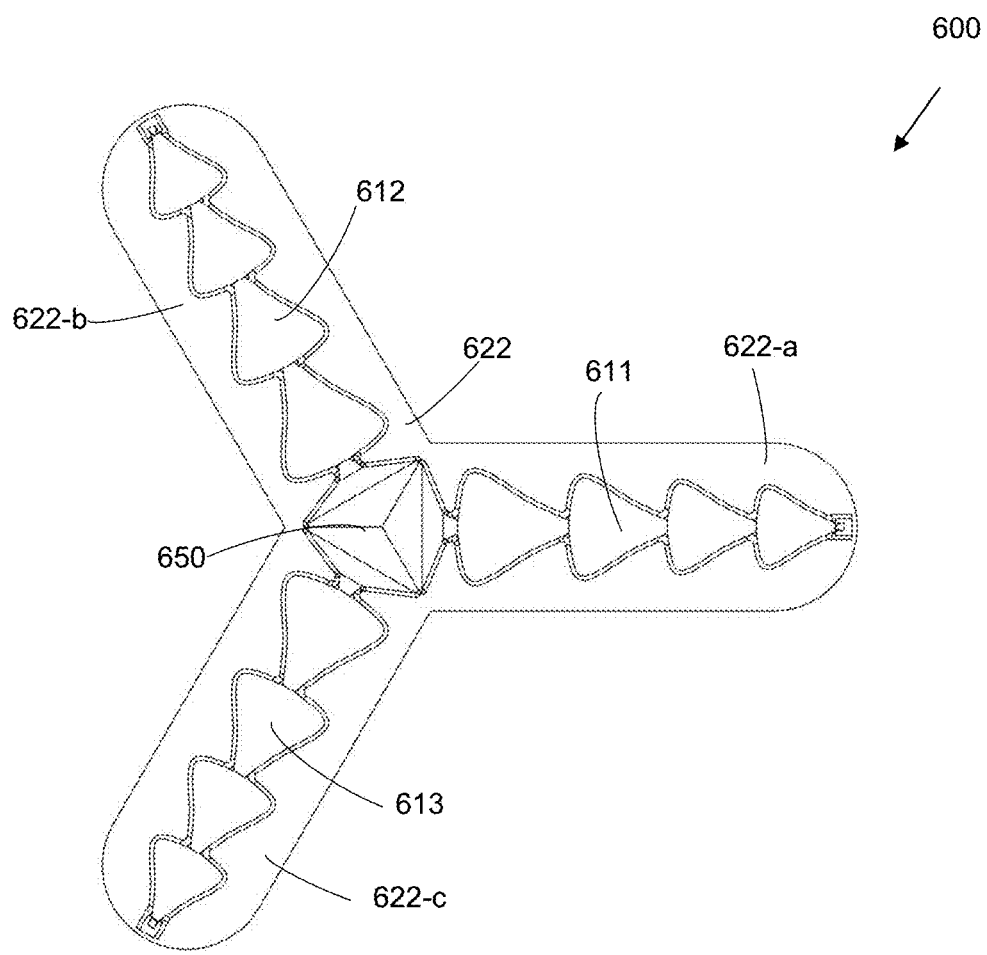
FIG. 10 shows a top view of another embodiment of the bandage.

FIG. 10 shows another embodiment of the bandage 600. Similar to the embodiment described in FIGS. 8A and 8B, with the difference that in this embodiment, the plurality of deformable hollow domes comprises twelve domes, with each of the first 611, second 612, and third set of domes 613 including four domes arranged linearly on the first 622-*a*, second 622-*b*, and third side 622-*c* of the adhesive section 622, respectively. The size of the domes in each set of domes 611, 612, and 613 reduces in the fluid flow direction which is outward from the central section 650 to the surrounding atmosphere.

Figure 11:
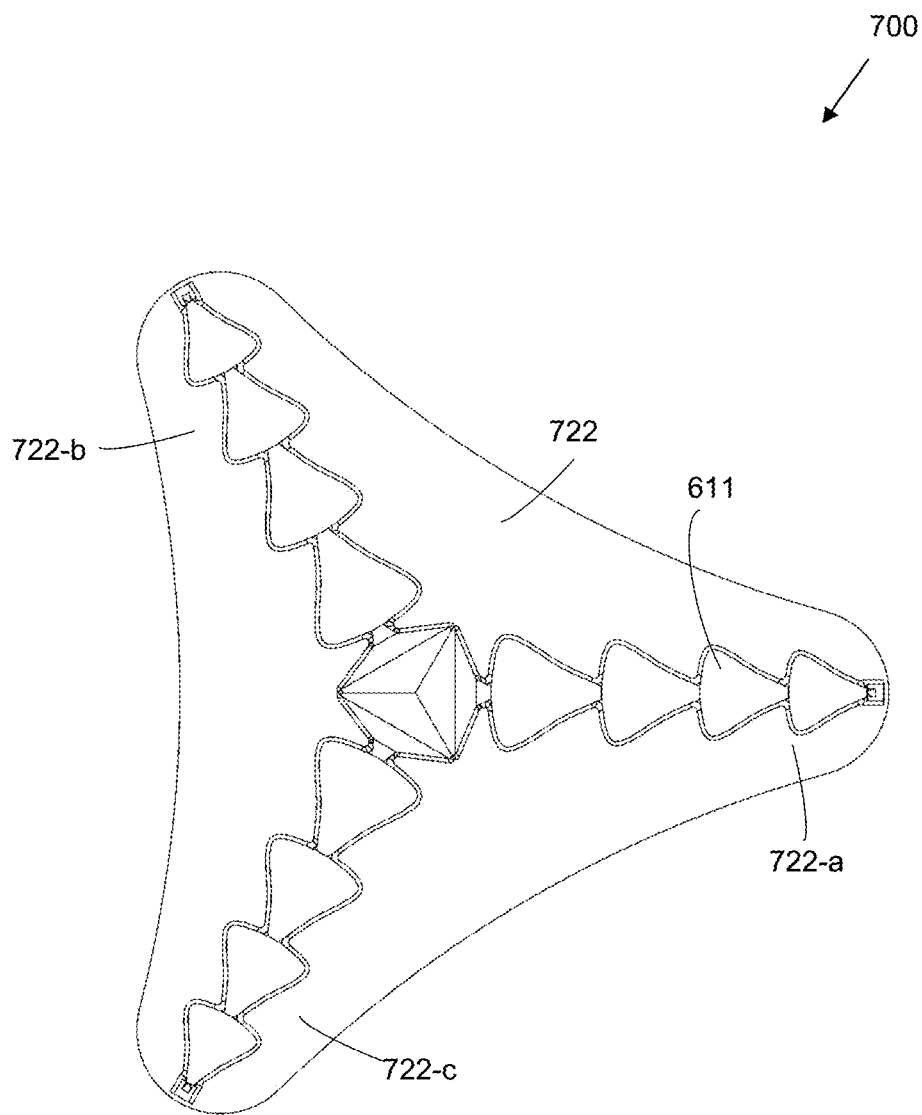
FIG. 11 shows a top view of another embodiment of the bandage.

FIG. 11 shows another embodiment of the bandage 700. Similar to the embodiment described in FIG. 10 with the difference that each of the three sides 722-*a*, 722-*b*, and 722-*c* of the adhesive section 722 is smoothly connected to the adjacent sides through curved, continuous transitions, forming a more expansive adhesive surface increasing the overall surface area of the adhesive section 722.

Figure 12A:
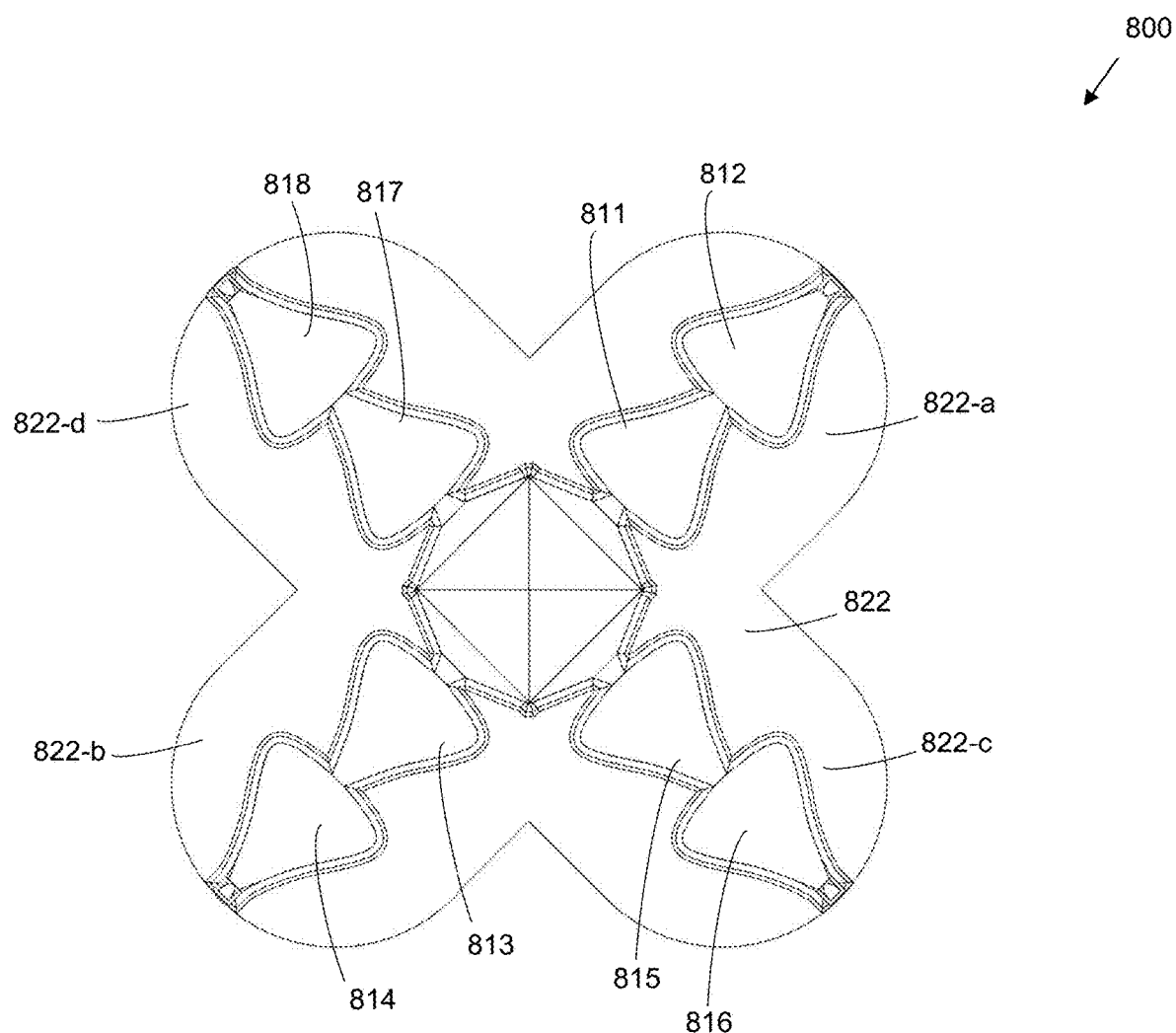
FIG. 12A shows a top view of another embodiment of the bandage.
Figure 12B:
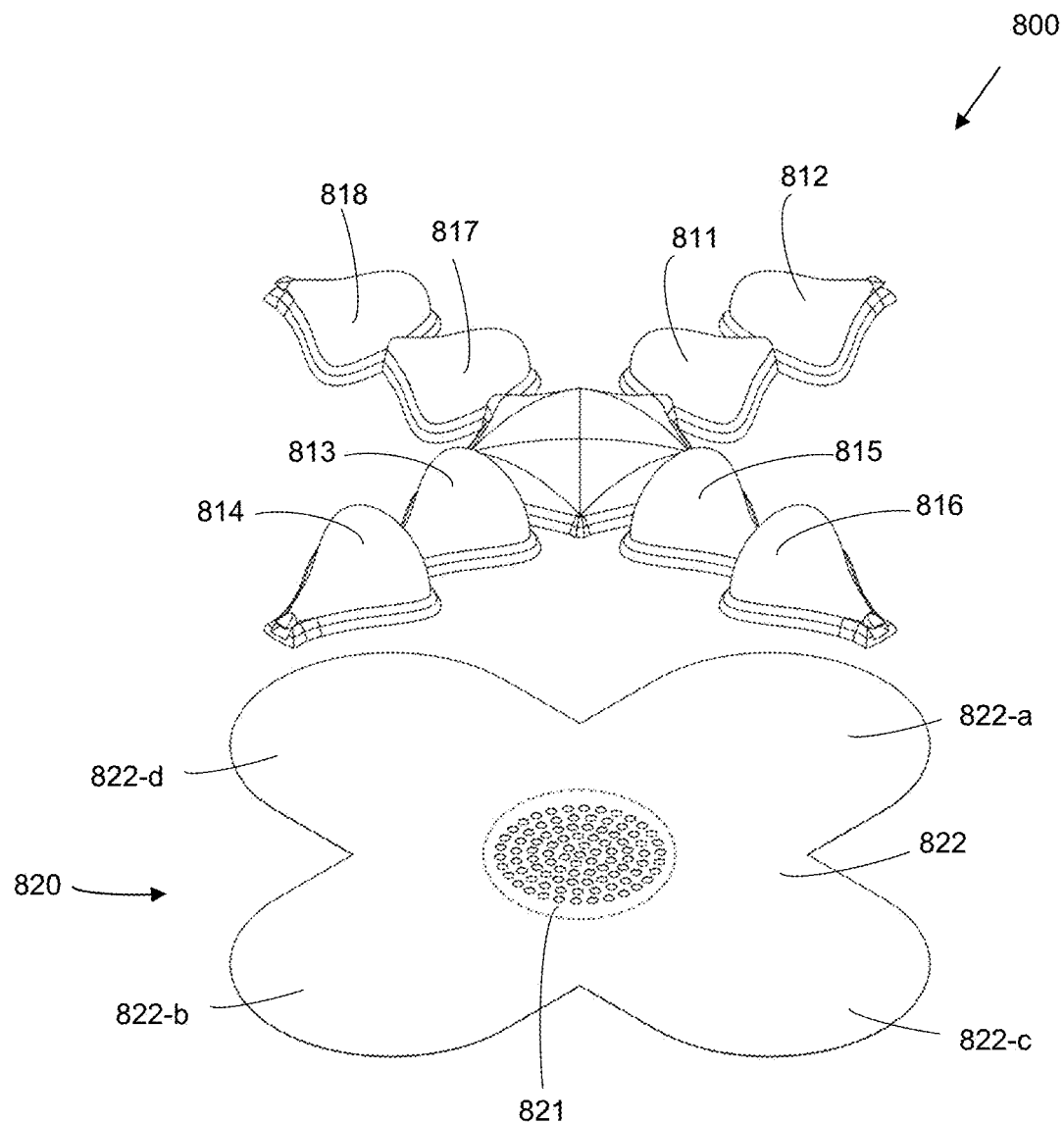
FIG. 12B shows an exploded view of another embodiment of the bandage.

FIGS. 12A, and 12B show top view and an exploded view of another embodiment of the bandage 800, respectively. In this embodiment, the adhesive section 822 comprises four sides: a first side 822-*a*, a second side 822-*b*, a third side 822-*c*, and a fourth side 822-*d* with each side extending outward from the contacting section 821. In this configuration, the bottom layer 820 forms a Greek cross arrangement with the contacting section 821 positioned in the middle of the bottom layer 820, the first side 822-*a* and the second side 822-*b* are aligned with respect to each other and the third side 822-*c* and the fourth side 822-*d* are aligned with respect to each other and cross aligned with respect to the first side 822-*a* and the second side 822-*b*. The plurality of deformable hollow domes comprises four set of domes: a first set of domes 811 and 812, a second set of domes 813 and 814, a third set of domes 815 and 816, and a fourth set of domes 817 and 818 arranged on the first 822-*a*, second 822-*b*, third 822-*c*, and fourth side 822-*d* of the contacting section 822, respectively. In one embodiment of the bandage, the plurality of deformable hollow domes comprises eight domes 811-818, with each set of domes including two domes.

Figure 13:
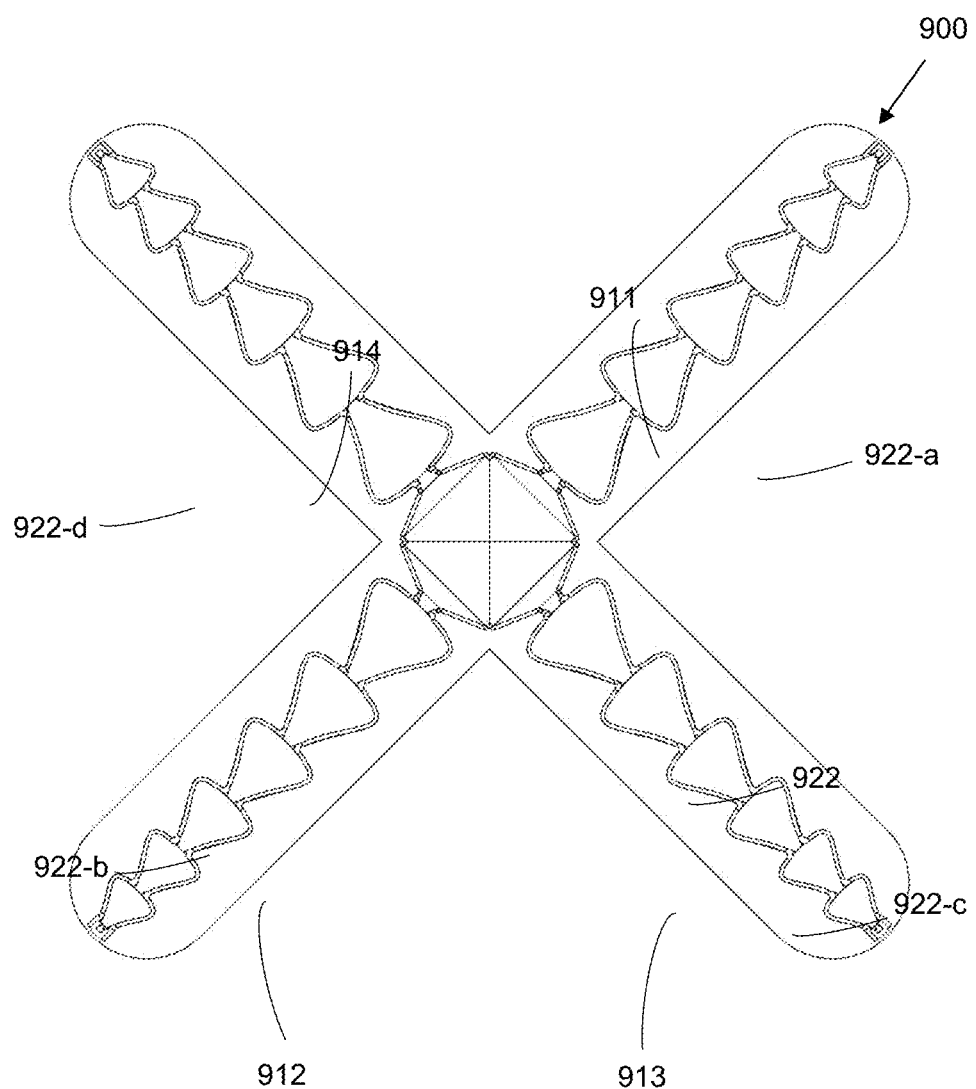
FIG. 13 shows a top view of another embodiment of the bandage.

FIG. 13 shows top view of another embodiment of the bandage 900. Similar to the embodiment described in FIGS. 12A and 12B, with the difference that in this embodiment, the plurality of deformable hollow domes comprises twenty-four domes, with each of the first 911, a second 912, a third 913, and a fourth set of domes 914 including six domes arranged linearly on the first 922-*a*, second 922-*b*, third 922-*c*, and fourth side 922-*d* of the adhesive section, respectively. The size of the domes in each set of domes 911, 912, 913, and 914 reduces in the fluid flow direction.

Figure 14:
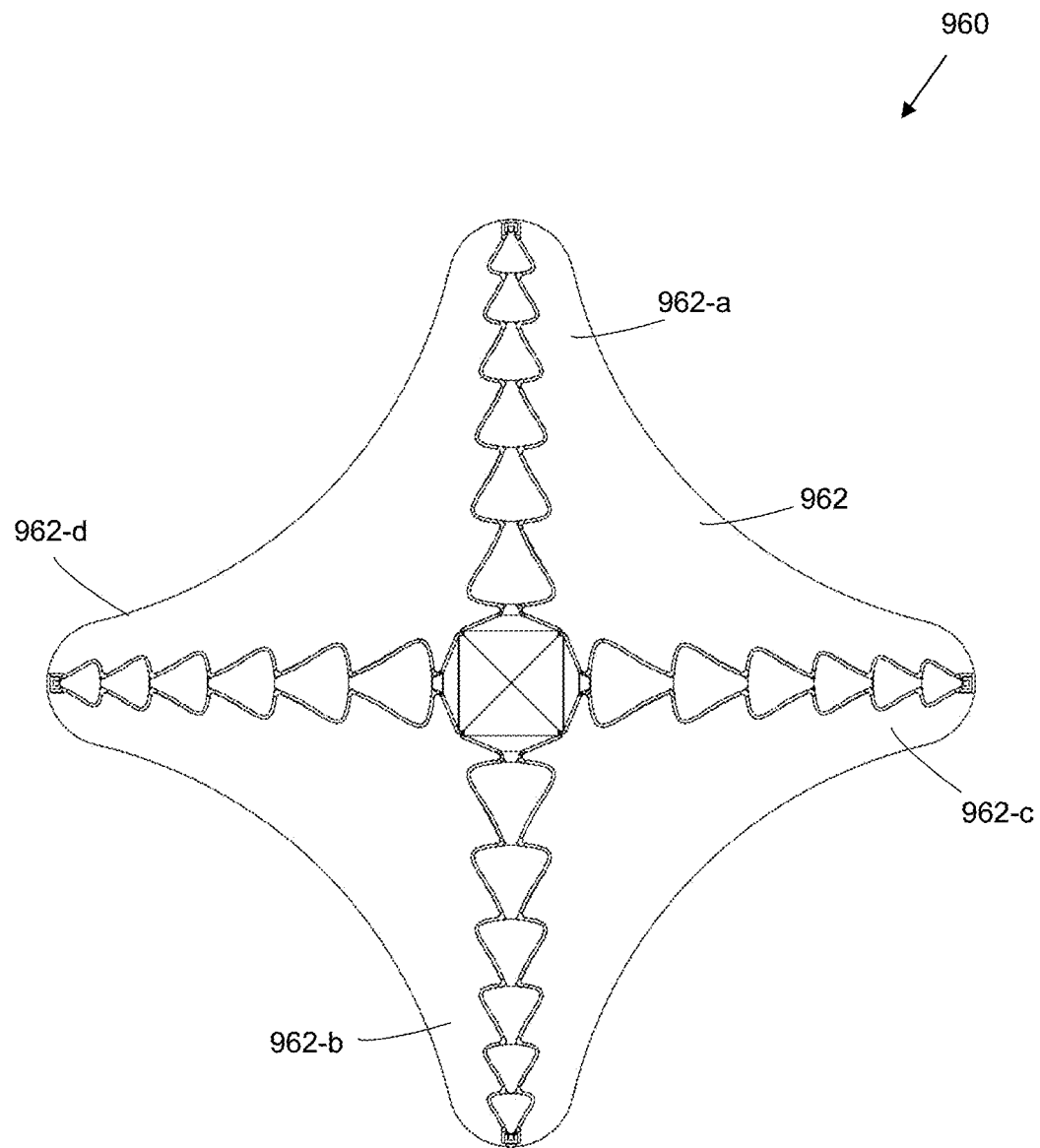
FIG. 14 shows a top view of another embodiment of the bandage.

FIG. 14 shows top view of another embodiment of the bandage 960. This embodiment is similar to the embodiment described in 13, with the difference that in this design each of the first 962-*a*, second 962-*b*, third 962-*c*, and fourth side 962-*d* of the adhesive section 962 is smoothly connected to the adjacent sides through curved, continuous transitions, forming a more expansive adhesive surface increasing the overall surface area of the adhesive section 962.

Figure 15:
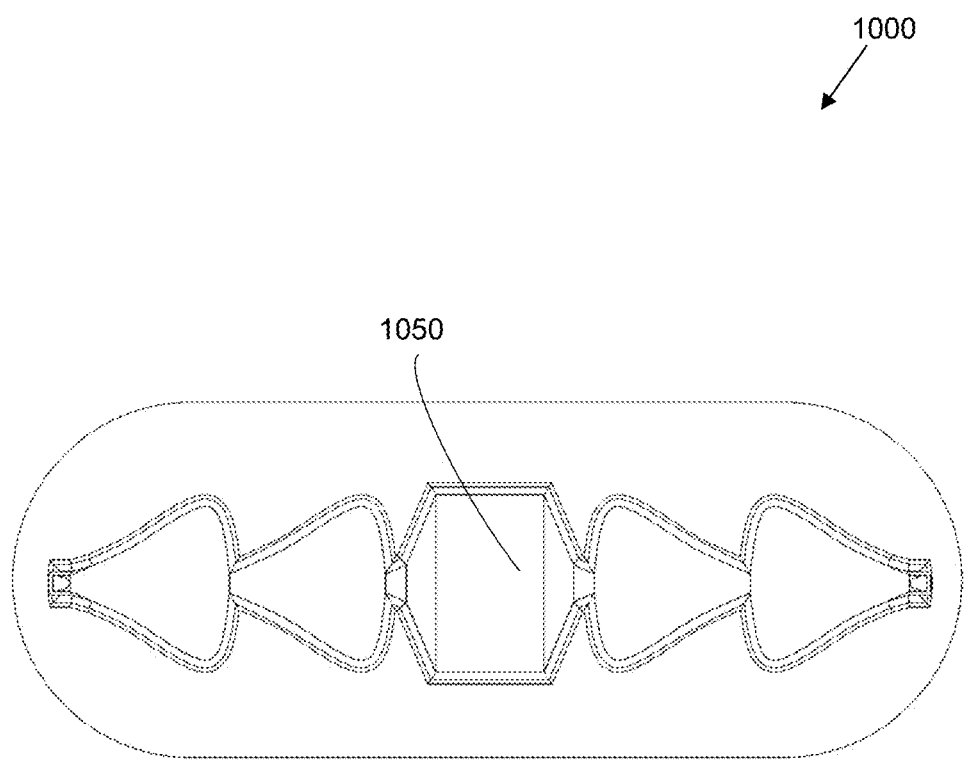
FIG. 15 shows a top view of another embodiment of the bandage.
Figure 16:
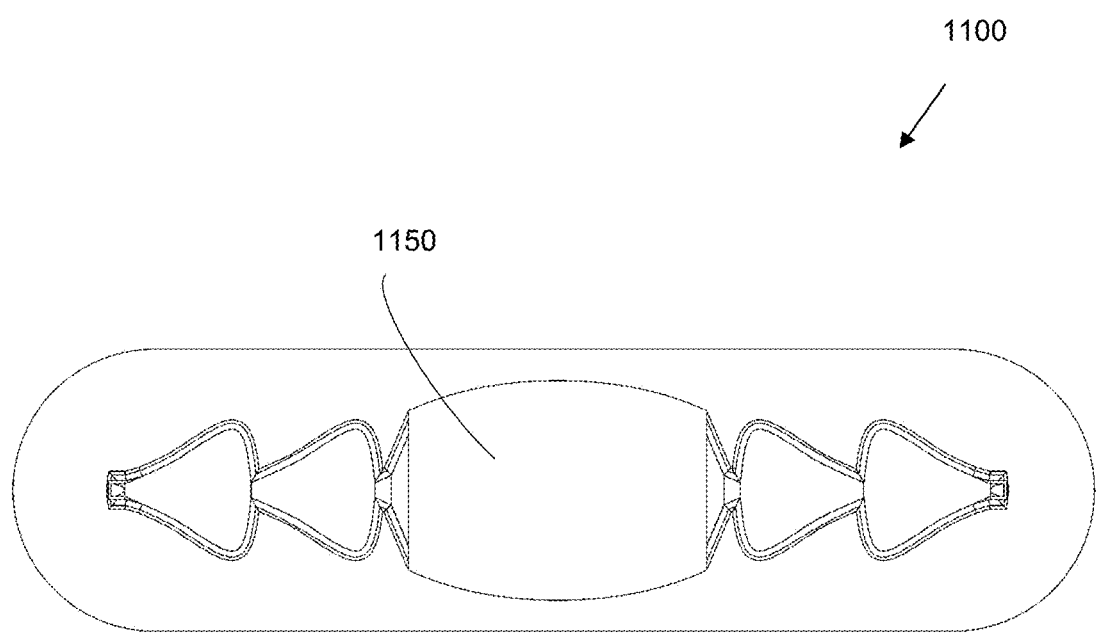
FIG. 16 shows a top view of another embodiment of the bandage.
Figure 17:
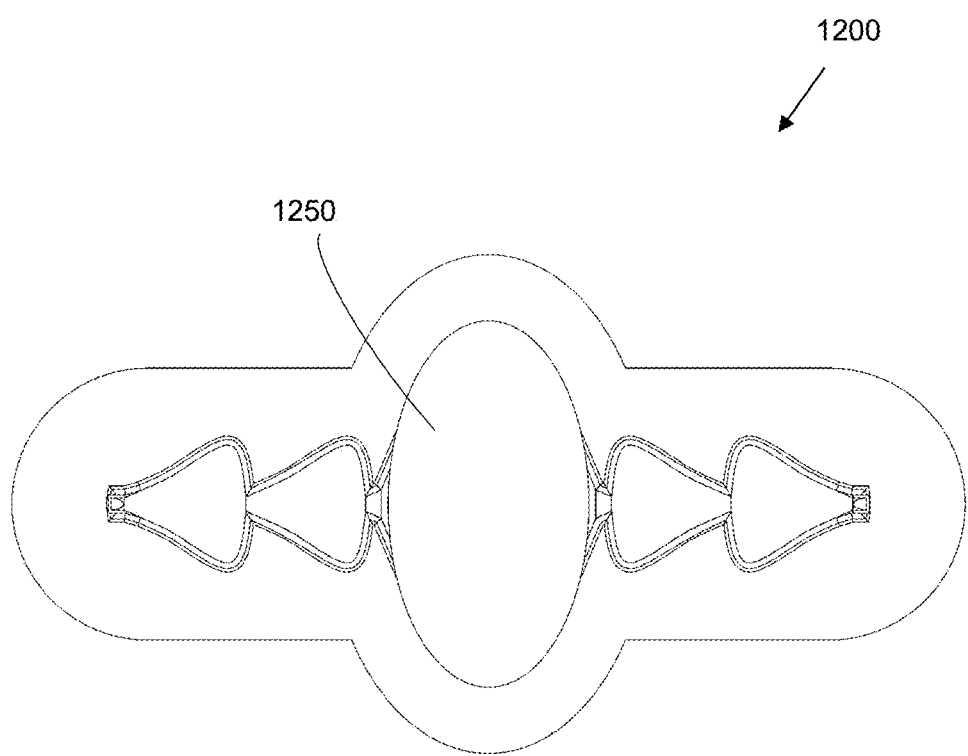
FIG. 17 shows a top view of another embodiment of the bandage.
Figure 18:
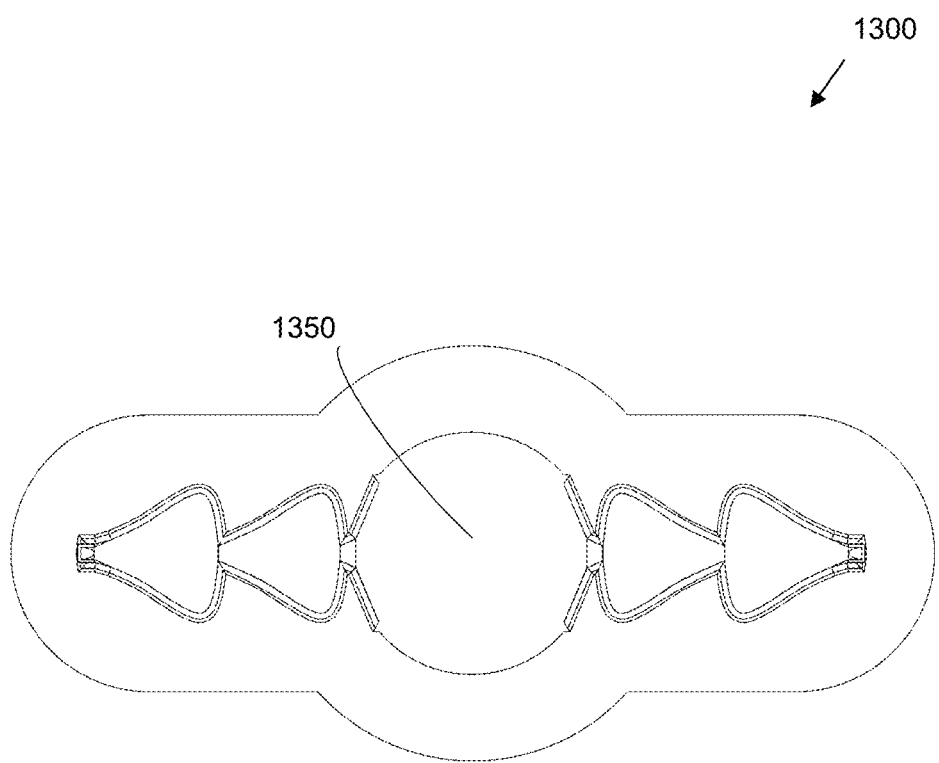
FIG. 18 shows a top view of another embodiment of the bandage.

FIGS. 15, 16, 17, and 18 show other embodiments of the bandage. These embodiments are similar to the first embodiment of the bandage described in FIGS. 1A-D, with the difference that the central sections vary in size and shape to cover wounds of different sizes and shapes. FIG. 15 shows the embodiment of the bandage 1000 with a larger hexagonal-based central section 1050 compared to the first embodiment of the device. In another embodiment, the bandage 1100 can have an oval-based central section 1150 positioned so that its longer diameter is parallel to the bandage 1000 length (FIG. 16). In another embodiment, the bandage 1200 can also have an oval-based central section 1250 positioned so that its shorter diameter is parallel to the bandage 1200 length (FIG. 17). In another embodiment, the bandage 1300 can have a circular-based central section 1350 (FIG. 18).

Figure 19:
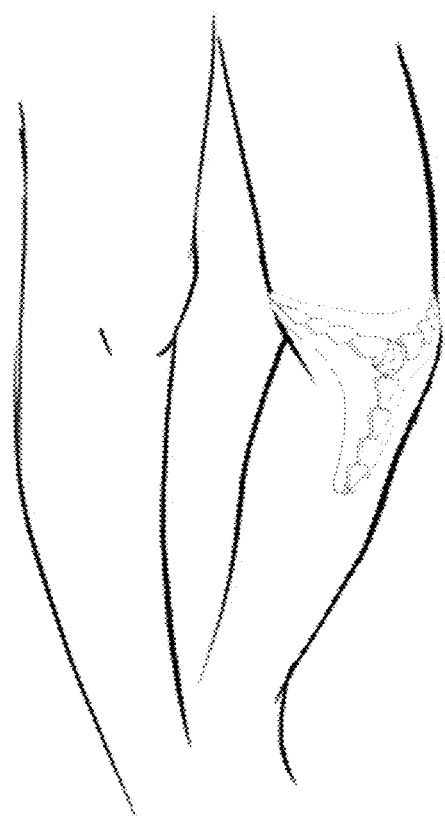
FIG. 19 shows one embodiment of the invention in use.

FIG. 19 shows one embodiment of the invention in use, where the bandage is positioned on the user's knee.

The invention claimed is:

1. A bandage, comprising:
   a) a bottom layer having a contacting section to be placed on top of a wound and an adhesive section to stick to skin surrounding the wound, wherein a wound dressing is attached to a bottom side of the contacting section and a plurality of apertures or an open section in the contacting section to allow a fluid out of the wound and into the bandage;
   b) a top layer, comprising:
      I. a central section immediately above the contacting section of the bottom layer defining an open cavity space;
      II. a plurality of deformable hollow domes immediately above the adhesive section of the bottom layer, each deformable hollow dome defining an interior space, wherein the plurality of the deformable hollow domes are made of a resilient material that return to their original shapes if deformed, and
      III. a plurality of one-way valves integrated into the bandage, comprising:
         i. at least a central one-way valve connecting the open cavity space of the central section to the interior space of at least one of the plurality of deformable hollow domes;
         ii. at least an intermediate one-way valve connecting the interior space of two adjacent deformable hollow domes, and
         iii. at least an exiting one-way valve connecting the interior space of at least one of the deformable hollow domes to a surrounding atmosphere;
      wherein the plurality of one-way valves are configured to provide a one-way fluid flow defining a flow direction from the open cavity space of the central section to the surrounding atmosphere through the plurality of deformable hollow domes and prevent a reverse fluid flow;
      whereby, by manually deforming the domes and squeezing air out of each dome, and when each dome returns to its original shape, a vacuum is drawn over the wound, thereby providing a negative pressure wound therapy over the wound, and whereby when a pressure differential between the pressure inside of each dome and an atmospheric pressure is below a predetermined threshold, said dome returns to its fully expanded configuration, and when the pressure differential is above the predetermined threshold, said dome remains in deformed configuration.

2. The bandage of claim 1, wherein each dome has a substantially semi-conical shape having its apex positioned on the downstream side of the one-way fluid flow and its base on the upstream side of the one-way fluid flow.

3. The bandage of claim 1, wherein each dome has a size, and the sizes of the plurality of deformable domes reduces in the flow direction with the largest dome being adjacent to the central section and the smallest dome being adjacent the surrounding atmosphere through the exiting one-way valve.

4. The bandage of claim 1, wherein said plurality of deformable hollow domes are positioned in a linear or a cross-linear alignment on the adhesive section.

5. The bandage of claim 1, wherein said plurality of deformable hollow domes comprising of a first set of domes on a first side of the adhesive section, and a second set of domes on a second side of the adhesive section, wherein the first set and the second set of domes are in linear alignment with respect to each other.

6. The bandage of claim 1, wherein said plurality of deformable hollow domes comprising of a first set of domes on a first side of the adhesive section, a second set of domes on a second side of the adhesive section, and a third set of domes on a third side of the adhesive section.

7. The bandage of claim 6, further having a fourth set of domes on a fourth side of the adhesive section.

8. The bandage of claim 7, wherein the third set and the fourth set of domes are in linear alignment with respect to each other and are in cross aligned with the first and second set of domes.

9. The bandage of claim 1, wherein the plurality of deformable hollow domes comprises of 2, 4, 6, 8, 12, 16 or 24 domes.

10. The bandage of claim 1, wherein each one-way valve is placed at a lower periphery of each dome.

11. The bandage of claim 1, wherein an operating pressure of the plurality of one-way valves increases in the flow direction with the valves with smallest operating pressure connecting the central section to one or more domes and the valves with biggest operating pressure connecting one or more domes to surrounding atmosphere.

12. The bandage of claim 1, wherein the dressing comprising of a liquid absorbing material to absorb wound exudate and liquids that come out of the wound.

13. The bandage of claim 1, wherein the central section of the top layer is made of a stiff material to keep an open cavity space above the wound.

14. The bandage of claim 1, wherein the size and the number of the domes are configured to provide a vacuum negative pressure of between 30 mm Hg and about 120 mmHg.

15. The bandage of claim 1, wherein one or more of the plurality of the deformable domes are filled with a fluid absorbing foams or superabsorbent particles or wicking fibers.

16. The bandage of claim 1, wherein the dressing is chosen from: absorbent dressing, antiseptic dressing, non-adherent dressing, water dressing, absorbable matrix, gauze, foam, or combinations thereof.

17. The bandage of claim 1, wherein the plurality of the domes and the bottom layer are chosen from: rubber, silicone, silicone blends, silicone substitutes, polyester, vinyl, polyvinyl chloride, polystyrene, polypropylene, polyurethane, polyimide, polyethylene napthalate, polycarbonates, polyester-polycarbonate blends, or a similar polymer, or combinations of all said materials.

18. The bandage of claim 1, wherein each dome has a non-uniform thickness with the periphery of each dome having a larger thickness and the top of each dome having a smaller thickness to facilitate reshaping.

19. The bandage of claim 18, wherein the larger thickness periphery of the domes is configured to restore the dome's shape under a predetermined pressure.

20. The bandage of claim 19, wherein the predetermined pressure ranges between 50 and 120 mmHg.

* * * * *